(12) United States Patent
Gephart et al.

(10) Patent No.: US 8,636,778 B2
(45) Date of Patent: Jan. 28, 2014

(54) WIDE ANGULATION COUPLING MEMBERS FOR BONE FIXATION SYSTEM

(75) Inventors: Matthew P. Gephart, Marquette, MI (US); Troy D. Knapp, Butler, IN (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 30 days.

(21) Appl. No.: 12/704,149

(22) Filed: Feb. 11, 2010

(65) Prior Publication Data

US 2010/0204735 A1  Aug. 12, 2010

Related U.S. Application Data

(60) Provisional application No. 61/151,564, filed on Feb. 11, 2009.

(51) Int. Cl.
*A61B 17/88* (2006.01)
(52) U.S. Cl.
USPC ........... 606/279; 606/267; 606/268; 606/86 A
(58) Field of Classification Search
USPC ....... 606/250–279, 103, 104, 86 A, 914–916, 606/99
See application file for complete search history.

(56) References Cited

U.S. PATENT DOCUMENTS

| | | |
|---|---|---|
| 4,805,602 A | 2/1989 | Puno et al. |
| 4,946,458 A | 8/1990 | Harms et al. |
| 4,950,269 A | 8/1990 | Gaines, Jr. |
| 5,042,982 A | 8/1991 | Harms et al. |
| 5,102,171 A | 4/1992 | Saetre |
| 5,176,680 A | 1/1993 | Vignaud et al. |
| 5,207,678 A | 5/1993 | Harms et al. |
| 5,226,766 A | 7/1993 | Lasner |
| 5,257,993 A | 11/1993 | Asher et al. |
| 5,261,913 A | 11/1993 | Marnay |
| 5,306,275 A | 4/1994 | Bryan |
| 5,346,493 A | 9/1994 | Stahurski et al. |
| 5,360,431 A | 11/1994 | Puno et al. |
| 5,368,594 A | 11/1994 | Martin et al. |
| 5,385,583 A | 1/1995 | Cotrel |
| 5,443,467 A | 8/1995 | Biedermann et al. |
| 5,492,442 A | 2/1996 | Lasner |
| 5,520,690 A | 5/1996 | Errico et al. |
| 5,545,228 A | 8/1996 | Kambin |
| 5,549,608 A | 8/1996 | Errico et al. |

(Continued)

FOREIGN PATENT DOCUMENTS

| | | |
|---|---|---|
| DE | 10005386 A1 | 8/2001 |
| EP | 0947174 A2 | 10/1999 |

(Continued)

*Primary Examiner* — Jan Christopher Merene
(74) *Attorney, Agent, or Firm* — Fitch, Even, Tabin & Flannery LLP

(57) ABSTRACT

A coupling assembly is provided with a yoke device that allows an anchor member secured thereto to rotate in a turret-like manner with respect to an elongate member secured by the yoke in addition to allowing the anchor member to pivot away from the central axis of the yoke. A first yoke member holds the elongate member and is rotatably coupled to a second yoke member that holds a bone anchor. A combination of rotation of the second yoke member and pivoting of the anchor member allows the anchor to be positioned in a wide variety of orientations with respect to the yoke device and elongate member.

8 Claims, 23 Drawing Sheets

(56) References Cited

U.S. PATENT DOCUMENTS

| | | |
|---|---|---|
| 5,586,984 A | 12/1996 | Errico et al. |
| 5,628,740 A | 5/1997 | Mullane |
| 5,630,817 A | 5/1997 | Rokegem et al. |
| 5,669,911 A | 9/1997 | Errico et al. |
| 5,672,176 A | 9/1997 | Biedermann et al. |
| 5,681,319 A | 10/1997 | Biedermann et al. |
| 5,683,392 A | 11/1997 | Richelsoph et al. |
| 5,690,630 A | 11/1997 | Errico et al. |
| 5,702,393 A | 12/1997 | Pfaifer |
| 5,728,098 A | 3/1998 | Sherman et al. |
| 5,733,285 A | 3/1998 | Errico et al. |
| 5,810,819 A | 9/1998 | Errico et al. |
| 5,817,094 A | 10/1998 | Errico et al. |
| 5,863,293 A | 1/1999 | Richelsoph |
| 5,879,350 A | 3/1999 | Sherman et al. |
| 5,885,286 A | 3/1999 | Sherman et al. |
| 5,910,142 A | 6/1999 | Tatar |
| 5,954,725 A * | 9/1999 | Sherman et al. ............... 606/78 |
| 5,961,517 A | 10/1999 | Biedermann et al. |
| 5,964,760 A | 10/1999 | Richelsoph |
| 5,989,250 A | 11/1999 | Wagner et al. |
| 5,997,539 A | 12/1999 | Errico et al. |
| 6,010,503 A | 1/2000 | Richelsoph et al. |
| 6,043,917 A | 3/2000 | Sonderegger et al. |
| 6,063,090 A | 5/2000 | Schlapfer |
| 6,132,432 A | 10/2000 | Richelsoph |
| 6,187,005 B1 | 2/2001 | Brace et al. |
| 6,254,602 B1 | 7/2001 | Justis |
| 6,280,442 B1 | 8/2001 | Barker et al. |
| 6,296,642 B1 | 10/2001 | Morrison et al. |
| 6,355,040 B1 | 3/2002 | Richelsoph et al. |
| RE37,665 E | 4/2002 | Ralph et al. |
| 6,371,957 B1 | 4/2002 | Amrein et al. |
| 6,379,356 B1 | 4/2002 | Jackson |
| 6,402,752 B2 | 6/2002 | Schaffler-Wachter et al. |
| 6,451,021 B1 | 9/2002 | Ralph et al. |
| 6,478,797 B1 | 11/2002 | Paul |
| 6,485,491 B1 | 11/2002 | Farris et al. |
| 6,485,492 B1 | 11/2002 | Halm et al. |
| 6,488,681 B2 | 12/2002 | Martin et al. |
| 6,565,565 B1 | 5/2003 | Yuan et al. |
| 6,660,004 B2 | 12/2003 | Barker et al. |
| 6,726,689 B2 | 4/2004 | Jackson |
| 6,736,820 B2 | 5/2004 | Biedermann et al. |
| 6,740,086 B2 | 5/2004 | Richelsoph |
| 6,755,289 B2 | 6/2004 | Weiss |
| 6,827,719 B2 | 12/2004 | Ralph et al. |
| 6,837,889 B2 | 1/2005 | Shluzas |
| 6,840,940 B2 | 1/2005 | Ralph et al. |
| 6,858,030 B2 | 2/2005 | Martin et al. |
| 6,918,911 B2 | 7/2005 | Biedermann et al. |
| 6,974,460 B2 | 12/2005 | Carbone et al. |
| 7,022,122 B2 | 4/2006 | Amrein et al. |
| RE39,089 E | 5/2006 | Ralph et al. |
| 7,066,937 B2 | 6/2006 | Shluzas |
| 7,081,117 B2 | 7/2006 | Bono et al. |
| 7,087,057 B2 | 8/2006 | Konieczynski et al. |
| 7,090,674 B2 | 8/2006 | Doubler et al. |
| 7,125,426 B2 | 10/2006 | Moumene et al. |
| 7,128,743 B2 | 10/2006 | Metz-Stavenhagen |
| 7,144,396 B2 | 12/2006 | Shluzas |
| 7,163,539 B2 | 1/2007 | Abdelgany et al. |
| 7,198,627 B2 | 4/2007 | Bagga et al. |
| 7,211,086 B2 | 5/2007 | Biedermann |
| 7,947,065 B2 * | 5/2011 | Hammill et al. ............... 606/267 |
| 7,951,173 B2 * | 5/2011 | Hammill et al. ............... 606/269 |
| 8,002,806 B2 * | 8/2011 | Justis ............................ 606/264 |
| 8,236,035 B1 * | 8/2012 | Bedor ........................... 606/328 |
| 2002/0026193 A1 | 2/2002 | Barker et al. |
| 2002/0082602 A1 | 6/2002 | Biedermann et al. |
| 2002/0111626 A1 | 8/2002 | Ralph et al. |
| 2002/0116001 A1 | 8/2002 | Schafer et al. |
| 2003/0004511 A1 | 1/2003 | Ferree |
| 2003/0100896 A1 | 5/2003 | Biedermann et al. |
| 2003/0125741 A1 | 7/2003 | Biedermann et al. |
| 2003/0125742 A1 | 7/2003 | Yuan et al. |
| 2003/0171755 A1 | 9/2003 | Moseley et al. |
| 2003/0187433 A1 | 10/2003 | Lin |
| 2004/0097933 A1 | 5/2004 | Lourdel et al. |
| 2004/0143265 A1 * | 7/2004 | Landry et al. ................... 606/61 |
| 2004/0153077 A1 | 8/2004 | Biedermann et al. |
| 2004/0176766 A1 | 9/2004 | Shluzas |
| 2004/0193160 A1 | 9/2004 | Richelsoph |
| 2004/0210216 A1 | 10/2004 | Farris et al. |
| 2004/0225289 A1 | 11/2004 | Biedermann et al. |
| 2004/0249380 A1 | 12/2004 | Glascott |
| 2005/0049588 A1 | 3/2005 | Jackson |
| 2005/0049589 A1 | 3/2005 | Jackson |
| 2005/0080420 A1 * | 4/2005 | Farris et al. ..................... 606/61 |
| 2005/0096659 A1 | 5/2005 | Freudiger |
| 2005/0113830 A1 | 5/2005 | Rezach et al. |
| 2005/0119658 A1 | 6/2005 | Ralph et al. |
| 2005/0154391 A1 | 7/2005 | Doherty et al. |
| 2005/0187548 A1 | 8/2005 | Butler et al. |
| 2005/0192570 A1 * | 9/2005 | Jackson ........................... 606/61 |
| 2005/0203515 A1 * | 9/2005 | Doherty et al. ................. 606/61 |
| 2005/0222570 A1 * | 10/2005 | Jackson ........................... 606/72 |
| 2005/0228385 A1 | 10/2005 | Iott et al. |
| 2005/0261687 A1 * | 11/2005 | Garamszegi et al. ........... 606/61 |
| 2005/0267472 A1 | 12/2005 | Biedermann et al. |
| 2005/0277924 A1 | 12/2005 | Roychowdhury |
| 2005/0277927 A1 | 12/2005 | Guenther et al. |
| 2006/0004357 A1 | 1/2006 | Lee et al. |
| 2006/0025767 A1 | 2/2006 | Khalili |
| 2006/0084995 A1 | 4/2006 | Biedermann et al. |
| 2006/0089643 A1 | 4/2006 | Mujwid |
| 2006/0096659 A1 | 5/2006 | Reusche et al. |
| 2006/0129149 A1 | 6/2006 | Iott et al. |
| 2006/0149241 A1 | 7/2006 | Richelsoph et al. |
| 2006/0149244 A1 | 7/2006 | Amrein et al. |
| 2006/0155278 A1 | 7/2006 | Warnick |
| 2006/0161152 A1 | 7/2006 | Ensign et al. |
| 2006/0161153 A1 | 7/2006 | Hawkes et al. |
| 2006/0173450 A1 | 8/2006 | Shibata |
| 2006/0173456 A1 | 8/2006 | Hawkes et al. |
| 2006/0200136 A1 * | 9/2006 | Jackson ........................... 606/61 |
| 2006/0235389 A1 | 10/2006 | Albert et al. |
| 2006/0241599 A1 | 10/2006 | Konieczynski et al. |
| 2006/0241600 A1 | 10/2006 | Ensign et al. |
| 2006/0276789 A1 | 12/2006 | Jackson |
| 2006/0276791 A1 | 12/2006 | Shluzas |
| 2006/0276792 A1 | 12/2006 | Ensign et al. |
| 2006/0293665 A1 | 12/2006 | Shluzas |
| 2006/0293666 A1 | 12/2006 | Matthis et al. |
| 2007/0043378 A1 * | 2/2007 | Kumar et al. ................. 606/104 |
| 2007/0055241 A1 | 3/2007 | Matthis et al. |
| 2007/0093817 A1 | 4/2007 | Barrus et al. |
| 2007/0093826 A1 | 4/2007 | Hawkes et al. |
| 2007/0093827 A1 | 4/2007 | Warnick |
| 2007/0270813 A1 * | 11/2007 | Garamszegi ..................... 606/61 |
| 2008/0015576 A1 * | 1/2008 | Whipple ......................... 606/60 |
| 2008/0045955 A1 | 2/2008 | Berrevoets et al. |
| 2008/0161859 A1 | 7/2008 | Nilsson |
| 2008/0177325 A1 | 7/2008 | Drewry et al. |
| 2008/0234757 A1 * | 9/2008 | Jacofsky et al. .............. 606/308 |
| 2009/0204155 A1 * | 8/2009 | Aschmann ..................... 606/264 |
| 2010/0262196 A1 * | 10/2010 | Barrus et al. .................. 606/308 |

FOREIGN PATENT DOCUMENTS

| | | |
|---|---|---|
| EP | 1741396 A1 | 1/2007 |
| EP | 1743584 A1 | 1/2007 |
| WO | 02054966 A2 | 7/2002 |
| WO | 2004047657 A2 | 6/2004 |
| WO | 2006047711 A2 | 5/2006 |
| WO | 2006072284 A1 | 7/2006 |
| WO | 2006116437 A2 | 11/2006 |
| WO | 2006119271 A2 | 11/2006 |
| WO | 2007040750 A2 | 4/2007 |
| WO | 2007040750 A3 | 4/2007 |
| WO | 2008059507 A1 | 5/2008 |

* cited by examiner

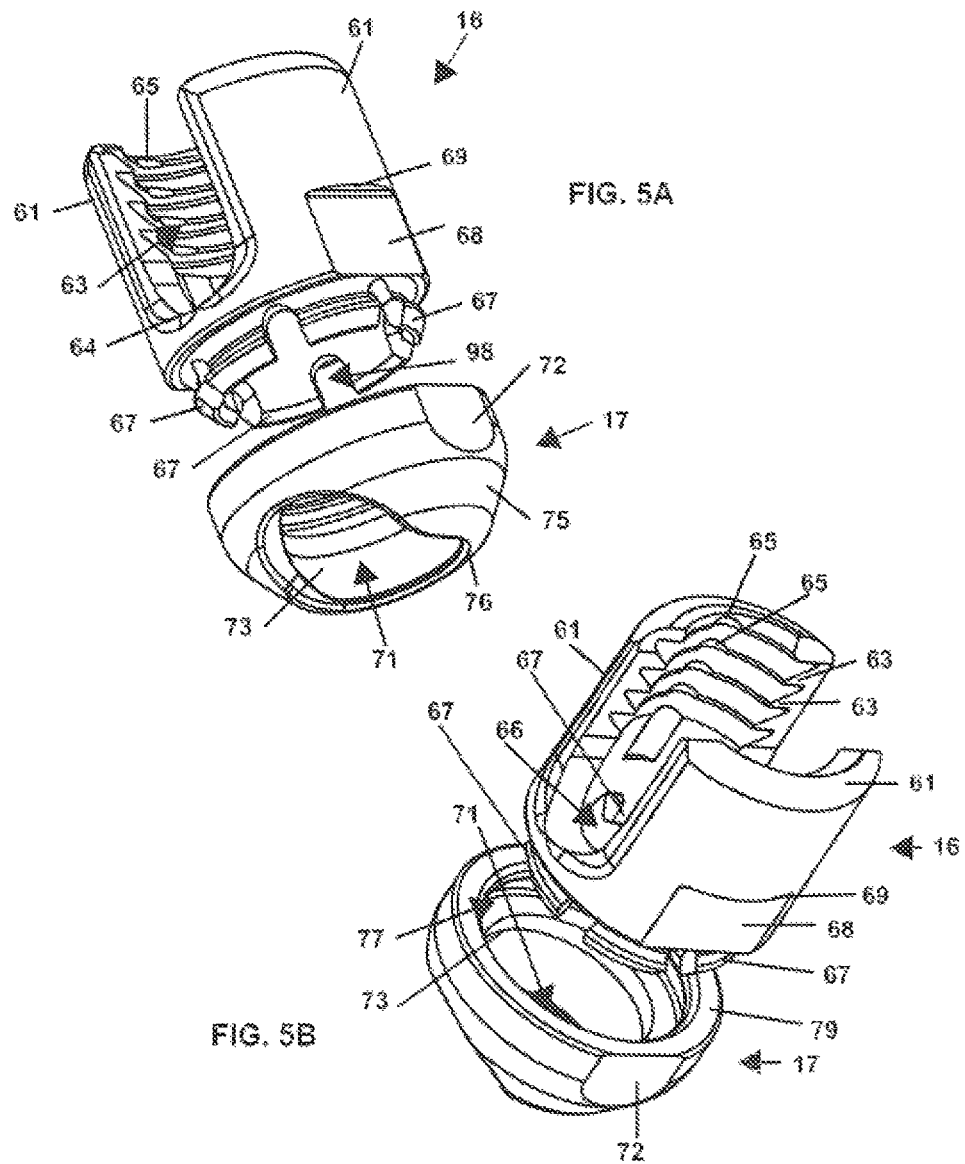

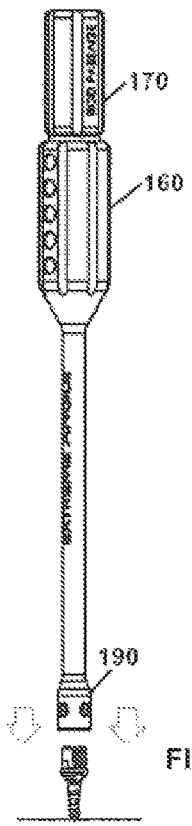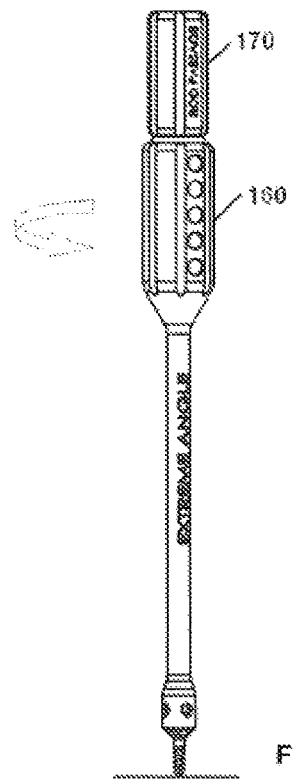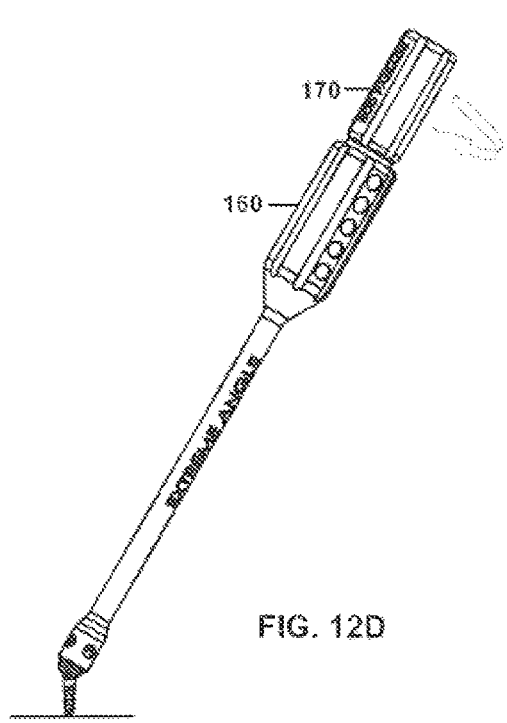
FIG. 12A
FIG. 12B
FIG. 12C
FIG. 12D

WIDE ANGULATION COUPLING MEMBERS FOR BONE FIXATION SYSTEM

CROSS-REFERENCE TO RELATED APPLICATIONS

This application claims the benefit of U.S. 61/151,564, filed Feb. 11, 2009.

FIELD OF THE INVENTION

The present systems and methods relate to bone fixation devices. More particularly, the present systems and methods provide for a low profile and wide angulation coupling assembly configured to facilitate the internal fixation of vertebral bodies.

BACKGROUND OF THE INVENTION

Normally, multi-directional and multi-axial bone anchor systems include an outwardly flared opening at the base of a coupling or yoke member through which an anchor member extends. For instance, in U.S. Pat. No. 7,141,051, a spherical or semi-spherical head at one end of the anchor member is trapped within the yoke housing, and a threaded shank portion of the anchor extends out from the bottom of the yoke housing through an outwardly flared opening. The angle of the outwardly directed flare of the opening in the yoke housing is normally configured to allow the screw shank to pivot to a desired angle in any direction around the axis of the yoke. When the patient's anatomy requires the anchor to be fixed at wider angles, the outwardly directed flare of the opening in the yoke housing is designed to be large enough to accommodate the wider angle without the edge of the opening interfering with the positioning of the screw shank or other anchor member. However, an increase in the angle and/or size of the opening in a yoke housing reduces the holding strength of the yoke, since increasing the size of the opening requires removal of material from the housing that would otherwise surround the head portion of the anchor member. Thus, accidental separation of the yoke and anchor member is more likely, increasing the potential for failure of the yoke in securely holding the anchor member therein.

SUMMARY OF THE INVENTION

In one form, a coupling or yoke device is provided with an opening in the coupling device that is sufficiently large to allow an anchor member, such as a pedicle screw or hook, to pivot to relatively extreme angles in a limited number of directions relative to a bottom portion of the coupling device, such as 45-60° or more away from a central axis of the coupling device. In order to provide a coupling assembly that allows the anchor member to pivot to extreme angles in multiple directions relative to a yoke device of the coupling assembly while still preserving the strength and structural integrity of the coupling assembly, the yoke may include a portion that swivels like a turret with respect to another portion. For instance, in one aspect of the invention a first or upper portion of the yoke device retains an elongate member, such as a spinal rod, that is used to connect multiple yokes for fixation of adjacent vertebrae. A second or lower portion of the yoke device may be configured to pivotably receive the anchor member, allowing the anchor member to pivot in a limited number of directions or planes with respect to the lower yoke portion. The second portion of the yoke device that holds the anchor member may be configured like a turret to rotate relative to the first portion while the orientation of the anchor member is varied with respect to the lower member. By configuring the first and second portions of the yoke device so that they are rotatable relative to one another, the anchor member may be pivoted to any desired direction and angle with respect to the elongate member without the necessity of providing significant clearance 360 degrees around the point at which the anchor member exits the yoke device.

The problems associated with multi-directional seating configurations are solved by the present coupling device, where instead of providing a large circular opening which permits extreme pivotal movement of an anchor in any direction, a portion of the yoke member is provided with a relatively small opening biased toward one side of the yoke that permits pivoting of the anchor member to an extreme angle in only a limited number of directions relative to the yoke axis. By combining this limited pivotal movement of the anchor member with rotational movement of at least one part of the yoke device, the anchor member may be fixed at any desired angle and direction with respect to a spinal rod or other elongate fixation member while firmly held within a sturdy yoke device. Although the description herein will refer primarily to pedicle screws, other anchor members, such as hook members, may be used in the invention presented herein.

In one form, a coupling device includes upper and lower yoke members with the upper yoke member having upper arms forming a channel to receive an elongate member. Opposite the upright arms, the upper yoke member has structures for securing the upper yoke member to the lower yoke member in a rotatable relationship, such as by snap-locking the upper yoke member to the lower yoke member. For instance, the upper yoke member may include downwardly directed tabs while the lower yoke member includes a corresponding annular recess into which the tabs of the upper yoke member may snap lock. Alternatively, the lower member may be provided with tabs that snap-lock into an annular recess of the upper member. The lower yoke member has an interior cavity having a seat for pivotably receiving the head portion of an anchor member. An opening is provided in the lower yoke member permitting a portion of the anchor member to extend therethrough and pivot with respect to the upper and lower yoke members. Preferably the opening is configured to allow the anchor member to pivot to a significant degree in a limited number of directions. For instance, the opening may be an elongate slot in a side of the lower yoke member opening at a bottom thereof, allowing the anchor to pivot away from the central axis of the yoke member in one direction to a desired magnitude. For instance, the slot may be configured to allow the anchor to pivot to an angle of 40°, 50°, 60°, 70°, 80°, 90°, or any other desired angle. In this regard, the lower opening of the lower yoke member is asymmetric in that it extends farther up along one side of the lower yoke member than the other.

In order to implant the coupling assembly in a patient, the shank of the anchor member is inserted through the lower opening in the lower yoke member. A driver or other instrument is used to fix the anchor member to the patient's vertebra with the head of the anchor member seated in the interior of the lower yoke member. Once the anchor member is secure, if not already connected, the upper yoke member is shifted toward the lower yoke member in order to secure the yoke members to one another. Thereafter, the lower yoke member and the upper yoke member rotatably coupled thereto can be pivoted relative to the anchor member, shifting the shank of the anchor member through the slot opening portion of the lower opening, and the upper yoke member is rotated relative to the lower yoke member as may be necessary to orient the upper yoke member for receiving the spinal rod therein. The elongate member may be secured in place within the upper yoke member by a cap member configured to lock to the upper yoke member. For instance, a threaded set screw, bayonet lock member, friction fitting plug, or other locking device may be used to secure the elongate member within the yoke. Tightening of the cap member exerts a downward force on the elongate member, which in turn exerts a locking force downward upon the anchor head, locking the anchor in place against the interior of the lower yoke member.

Optionally, a core insert member may be provided to fit between the head of the anchor member and the surface of the elongate member. The insert member may be configured to friction fit against interior surfaces of the yoke, the upper surface of the anchor member head, a lower surface of the elongate member, or a combination thereof.

Further, an instrument may be provided for separately manipulating the upper and lower yoke members. For instance, the instrument may have a first portion that secures the exterior of the lower yoke member and a second portion configured to fit into the rod channel to secure the upper yoke member, with the first and second instrument portions rotatable relative to one another in order to orient the upper and lower yoke members.

BRIEF DESCRIPTION OF THE DRAWINGS

FIGS. 5A-5D illustrate the upper and lower yoke members. FIG. 5A is a perspective view of the yoke members from below. FIG. 5B is a perspective view of the yoke members from above. FIG. 5C is a cross-sectional view of the yoke members separated from one another. FIG. 5D is a cross-sectional view of the assembled yoke members snap fit together.

FIGS. 12A-D demonstrate use of the instrument of FIGS. 8-11.

DETAILED DESCRIPTION OF THE PREFERRED EMBODIMENTS

In one aspect of the invention, a coupling assembly is provided with a two-part yoke device that allows the relative orientation between an anchor member and an elongate member to be widely varied. In prior systems, an anchor is often provided with a spherical or semi-spherical head that may pivot to various angles with respect to the coupling member in which it is retained. For instance, U.S. Pat. No. 7,141,051 illustrates in FIG. 3 thereof a coupling member that receives the head of a pedicle screw and allows the pedicle screw to pivot a relatively small amount away from the axis of a coupling member. This allows the pedicle screw to be fixed at an angle with respect to the central axis of the coupling member, instead of merely allowing the anchor to extend along the central axis. The ability of the anchor to pivot depends greatly upon the configuration of the coupling member or yoke, in that the opening in the yoke must be large enough to avoid interference with pivoting of the pedicle screw shank, but must also be small enough to prevent the pedicle screw head from exiting the bottom of the yoke.

Figure 22:
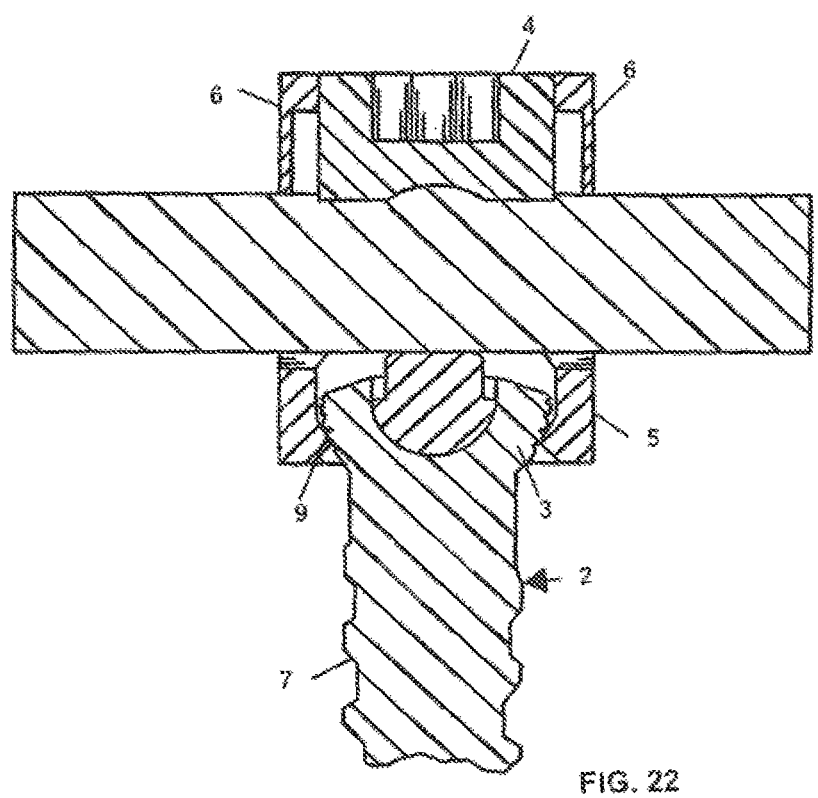
FIG. 22 is a cross-sectional view of a prior art coupling device.

FIG. 22 shows a prior art device, where a yoke member 5 pivotably receives a pedicle screw 2 with a head portion 3 of the screw having a semi-spherical lower surface. The screw head portion 3 is seated on a corresponding semi-spherical surface 9 of the interior of the yoke member 5. The yoke member 5 also receives an elongate member 8, such as a spinal rod. The elongate member is secured within the yoke 5 by a cap member 4 which is received in the yoke and locked into place by interaction between the cap member 4 and upwardly extending portions 6 of the yoke member. The rod 8 is received in only one orientation within the yoke member 5, so that altering the relative positioning between the rod 8 and the screw 2 is accomplished only by pivoting of the screw 2. The pivoting of the screw 2 is limited by the configuration of the yoke seat 4. As the shank 7 of the screw pivots away from the central axis of the yoke, it will abut the seat portion 4 of the yoke. However, if the size of the seat 4 is reduced to allow a larger opening that will permit more exaggerated pivoting of the screw 2, there is less and less material left to keep the head portion 3 of the screw 2 from being pulled through the opening in the bottom of the yoke.

The pedicle screw system 11 illustrated in FIGS. 1-4 is configured to allow the pivoting of an anchor member to a greater degree than allowed in the prior art. As shown in FIG. 1A, the yoke device 15 couples an elongate member such as spinal rod 18 to an anchor member such as the illustrated pedicle bone screw 12. The yoke device 15 includes an upper yoke member 16 and a lower yoke member 17. The upper yoke member 16 holds the spinal rod 18, which is secured in placed by a locking member that engages the upper yoke member 16. The lower yoke member 17 has a bottom opening 71 to allow the pedicle screw to pass through the yoke device for being secured to vertebral bone. The head of the pedicle screw is retained within the lower yoke member 17 with only the shank 25 of the pedicle screw passing through the opening 71 in the lower yoke member 17. Instead of enlarging a bottom circular opening in the yoke member, the illustrated device provides a yoke member 15 with an opening that allows pivoting of an anchor member, such as the illustrated pedicle bone screw 12, to a significant degree in only a finite number of directions relative to the opening. In the illustrated embodiment, pivoting is essentially limited to a single plane.

More specifically, the opening 71 in the lower yoke member 17 is configured so that it extends from a lower face of the lower yoke portion 17 to only one side face of the lower yoke portion via an elongate slot portion 71c thereof rather than extending radially outward from the center of the lower yoke portion to an equal distance in every direction. This allows the pedicle screw 12 to pivot an angular distance theta (Θ) away from a central axis 55 of the yoke device in one direction. The angular distance of pivoting (Θ) away from the yoke's central axis 55 is greater than that which would normally be allowed with prior art multi-axial pedicle screws. For instance, the slot opening portion 71c may allow the shank to pivot 60° or more away from the yoke axis 55. This greater magnitude of pivoting is possible because the pedicle screw 12 may pivot only in one or a limited number of directions due to the configuration of the slot opening 71. The lower yoke member has a cup-shaped generally annular wall 79 with opposite side portions 75 and an end portion 76 extending between the side portions 75 which limits the pivoting of the pedicle screw 12 in other directions, but at the same time serves to securely retain the screw head within the yoke device 15. Essentially, the screw head is surrounded on three sides and allowed to pivot toward its fourth, unbounded side.

In order to compensate for the loss of pivoting motion in one or more directions, the lower yoke portion 17 is rotatably coupled to the upper yoke portion 16 so that the direction of the opening 71 in the lower yoke portion may be varied with respect to the position of the upper yoke member 16 and the elongate member 18 held therein. Through this rotatable coupling, the pedicle screw 12 may be manipulated to pivot to an angle of theta (Θ) in any direction around the central yoke axis 55. The integrity of the coupling between the yoke and the screw can be comparable to, or even better than, conventional coupling assemblies, since the overall size of the lower opening in the yoke will usually be the same as or smaller than that of a conventional coupling member. The placement of the opening, however, is able to favor one side of the yoke due to the rotatability between upper and lower yoke members. The opening of the lower yoke member may be configured so that the angle (Θ) to which the anchor member pivots away from the yoke axis is set, for instance, at about 30°, 40°, 50°, 60°, 70°, 80°, 90° or even greater, or any angle therebetween which is far beyond that allowed by conventional multi-axial pedicle screw assemblies. Of course, the angle of pivoting may also be designed to be less than outlined above without deviating from the invention presented herein.

Figure 1A:
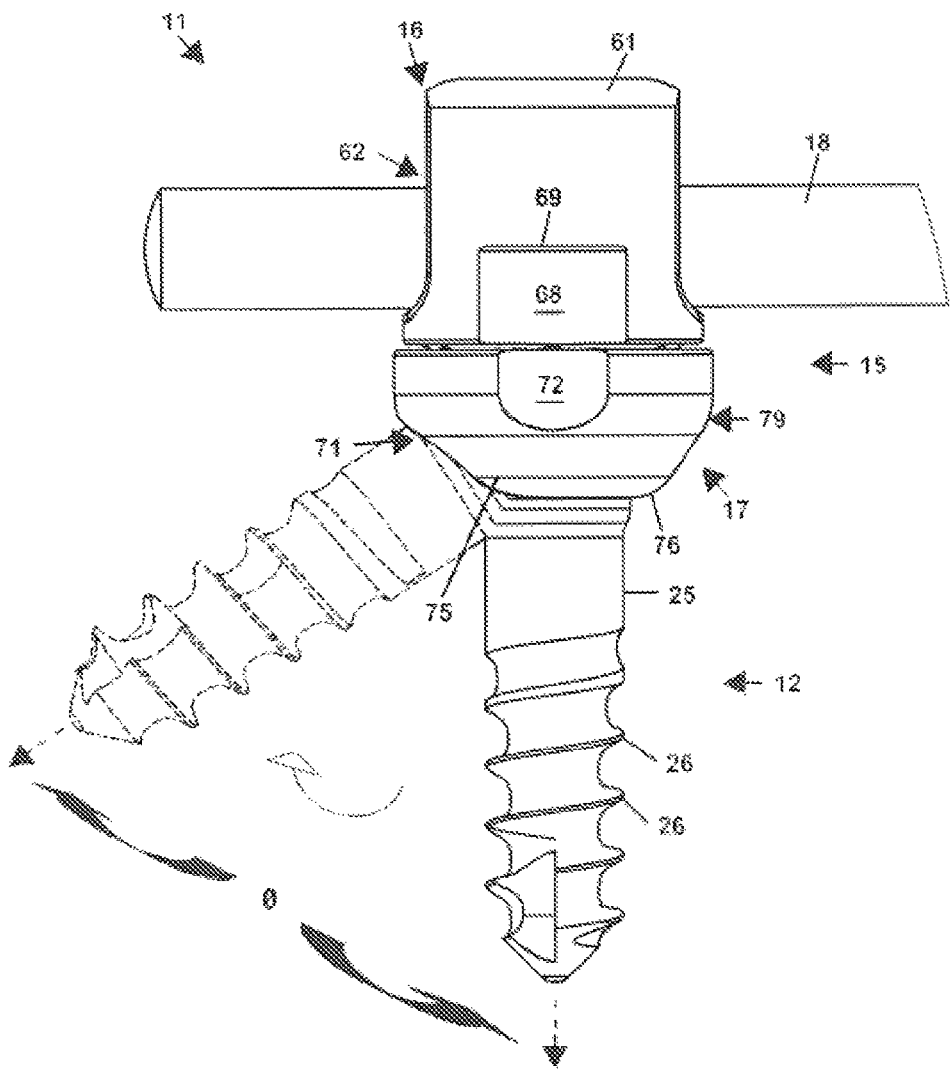
FIG. 1A is an elevational view of an exemplary coupling assembly of a pedicle screw device showing pivotability of the anchor member in one direction.
Figure 1B:
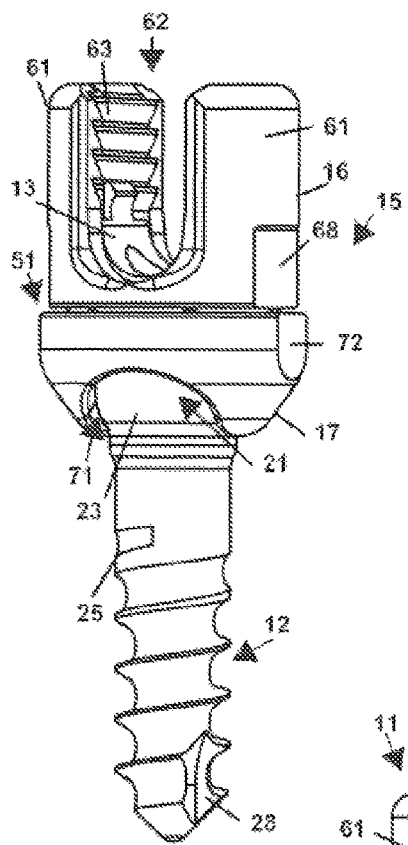
FIG. 1B is a three quarters perspective view of the coupling assembly of FIG. 1 showing a slot opening portion in a lower yoke member of the coupling assembly for pivoting of the anchor member thereof.

FIG. 1B shows the coupling device 15 of FIG. 1A from a three quarters view. From this view, it can be seen that the opening 71 in the lower yoke member 17 extends up one side of the lower yoke member 17. The upper yoke member 16 includes upwardly directed arms 61 which form a channel 62 therebetween. An elongate member is received in the channel 62 and locked in place by a cap member or other locking device.

In one form, threads 63 may be provided on the interior surfaces of the upwardly extending arms 61 in order to receive complementary threads of a locking cap member to lock the cap member into place, securing the spinal rod. Alternatively, the cap or other locking device may engage the exterior of the yoke or have other types of locking elements for engaging corresponding locking elements of the yoke member. A variety of locking devices for yoke devices are known, and may be combined with the present invention. For instance, the upper yoke member 16 may be configured to receive and lock with any of the locking caps disclosed in U.S. Pat. No. 7,141,051; U.S. Published Application No. 2007/0055235; U.S. Published Application No. 2008/0045955; U.S. Published Application No. 2007/0225711; and other locking devices for pedicle screw or hook assemblies. The contents of the aforementioned patents and publications are hereby fully incorporated by reference as if fully set forth herein.

In the illustrated embodiment, an insert member (which will be described in greater detail below) is disposed within the upper yoke member 16. The insert member 13 in the illustrated embodiment includes an upper surface that is complementary to the cylindrical outer surface of a spinal rod that is to be received in the channel 62. As will be described further below, the lower surface of the insert member 13 may be configured to bear against the head 21 of the pedicle screw 12.

A lower surface 23 of the pedicle screw head 21 may be seen through the anchor opening 71 in the view of FIG. 1B. The lower surface of the screw head bears against an interior seating surface of the lower yoke member 17. The shape and size of the pedicle screw head portion 21 prevent exit of the head portion 21 through the opening 71 in the lower yoke member. It should be noted that, while the pedicle screw head 21 is depicted as generally spherical or semi-spherical in the illustrated embodiment, due to the limited pivoting of the anchor the head 21 may alternatively be cylindrical, conical, disk shaped, or any other shape or configuration that allows pivoting of the screw shank 25 without being able to fully pass through the lower yoke opening 71.

Figure 1C:
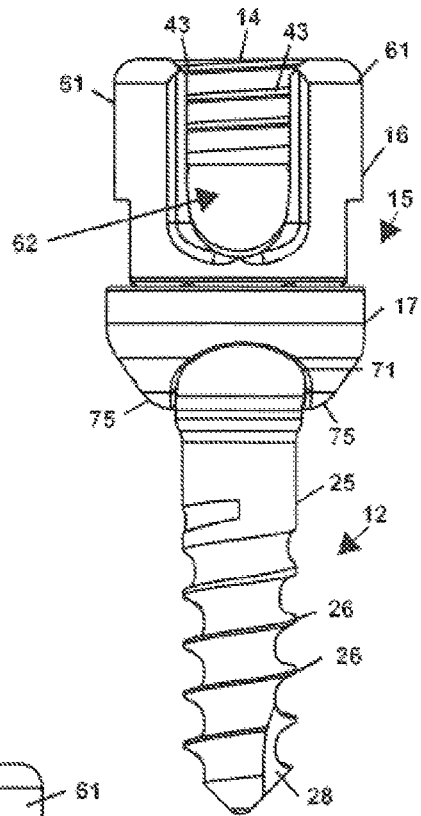
FIG. 1C is a front elevational view of the coupling assembly of FIGS. 1A and 1B.

FIG. 1C depicts the pedicle screw system of FIG. 1A from a front view. As can be seen, opening 71 allows pivoting of the pedicle screw shank 25 toward the viewer to a significant degree, but little pivotal movement is allowed to either side because side surfaces 75 of the lower yoke portion 17 interfere with any angular displacement of the screw shank and also block exit of the pedicle screw head portion 21 from the slot opening 71 of the lower yoke portion 17.

In FIG. 1C, a locking cap member 14 has been secured to the upper yoke portion 16. More specifically, a substantially cylindrically shaped cap member 14 with helical threading 43 has been rotated into place between upright arms 61 of the upper yoke portion 16. In order to receive the threaded cap member 14, the upper arms 61 of the upper yoke portion 16 are equipped with grooves or threading on their interior surfaces that are complementary to threading 43 on the cap member 14. Thus as the cap member is locked into place, the open end of channel 62 is blocked, preventing an elongate member or spinal rod placed therein from escaping from the upper yoke member.

Ideally the upper yoke member 16 and cap member 14 are configured so that as the cap member is locked in place, it bears down upon a spinal rod or other elongate member placed in the channel 62 in order to fully immobilize the rod or elongate member. The cap member 14 need not be threaded so long as it may be secured to the upper yoke member 16 and exert a locking force on the spinal rod or elongate member. For instance, the cap member may be an external nut with threading on its interior complementary to threading on the exterior of the yoke, or may be equipped with discrete flanges that operate to secure the cap member to the upright arm 61 of the upper yoke member 16. In addition, a cap member may instead be configured to be linearly inserted into the upper yoke member without rotation, either parallel or transverse to the primary axis of the yoke device 15. For instance, a cap member such as that shown in U.S. Patent Publication No. 2007/0225711, the contents of which are hereby fully incorporated herein, also may be adapted for use with the present invention, locking in place between the arms 61 of the upper yoke member 16 and a modified version of the insert member 13. The yoke device 15 may be readily modified to cooperate with various other styles of locking cap, as long as the cap is effective for fixing the position of a spinal rod or other elongate member with respect to the upper yoke member 16.

Figure 1D:
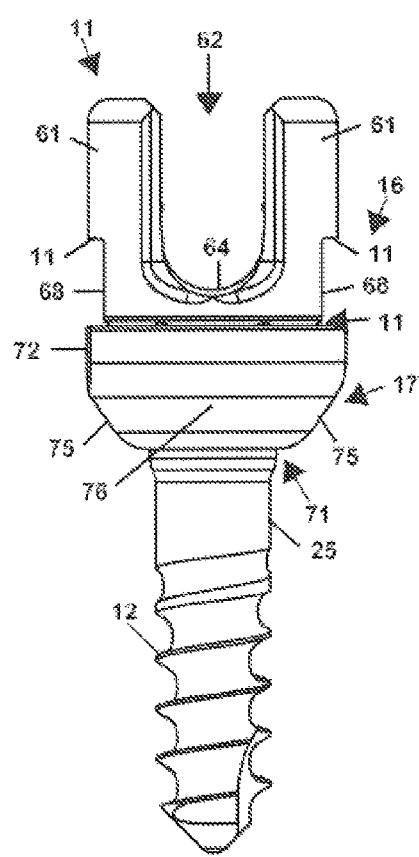
FIG. 1D is a rear elevational view of the coupling assembly showing the solid wall portion of the lower yoke member 180° from the slot opening portion.

FIG. 1D shows the rear plan view of the coupling device 11 of FIG. 1A with associated pedicle screw 12. From this perspective, opening 71 in the lower yoke portion 17 is not visible, because it extends from the bottom surface of the lower yoke portion to the far side of the lower yoke portion. However, due to rotatable coupling of lower yoke member 17 and upper yoke member 16 at yoke junction 51, the lower yoke member 17 may be rotated so that opening 71 faces in another direction, such as toward the viewer of FIG. 1D, without changing the orientation of upper yoke member 16. Other yoke structures are as described in FIGS. 1A-1C.

Figure 2A:
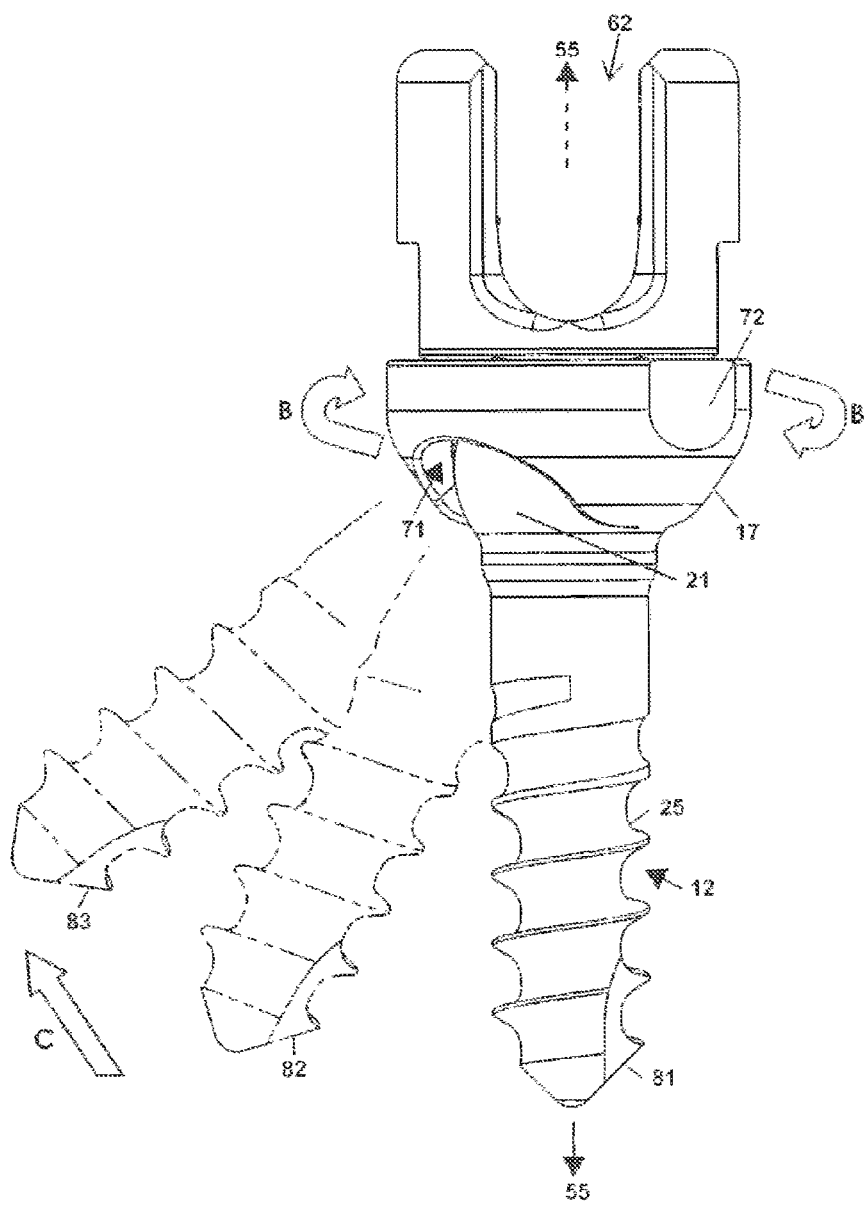
FIGS. 2A and 2B are elevational views of the coupling assembly showing the lower yoke member rotated to different positions relative to an upper rod receiving yoke member with the anchor member shown pivoted to different angles in phantom.
Figure 2B:
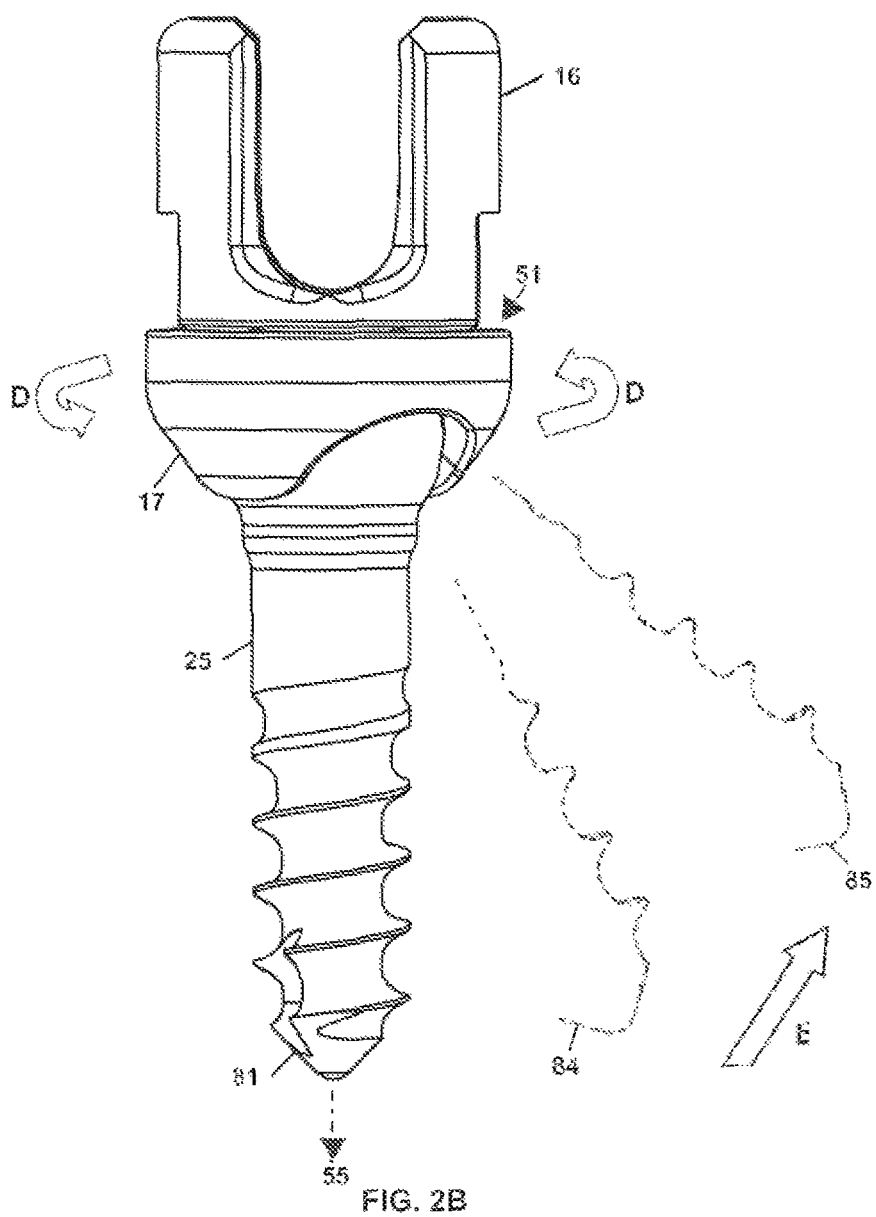

FIGS. 2A and 2B demonstrate how the rotatability of the assembly and pivotability of the pedicle screw 25 enable the screw to be positioned at a plurality of angles and directions with respect to a spinal rod. FIG. 2A is a view of a coupling device along the axis of the channel 62 in the upper yoke member 16. Arrows indicate that the lower yoke member 17 may be rotated with respect to the upper yoke member about the axis 55 of the yoke device. In FIG. 2A, the lower yoke member has been rotated in a clockwise direction B when viewed from above the yoke device.

Screw shank 25 is allowed to pivot to a significant degree only back and forth in a single plane because of the configuration of the slot opening 71, and therefore rotation of the lower yoke member 17 determines the direction of pivotability of the screw shank 12. The lower yoke member 17 is rotated so that opening 71 faces the direction in which the screw shank 25 is to be pivoted. Of course, the indicated pivotability of the screw shank is merely relative to the position of the yoke device, so that when the screw shank 12 is implanted into bone the orientation of opening 71 in lower yoke portion 17 actually determines in which direction the yoke device 15 may tilt relative to the stationary screw shank to accommodate a spinal rod. Although the head portion 21 of the pedicle screw may be of any shape and configuration, it is preferable that the head is generally spherical or otherwise configured to allow lower yoke portion 17 to rotate about the pedicle screw head portion 21 in addition to the pivoting movement. This allows the slot opening 71 to be oriented in different directions after screw shank 25 has been disposed in a vertebra without requiring further rotation of the screw. One or more flat surfaces 72 may be provided on the lower yoke portion 17 to provide grasping features that can be engaged by an instrument in order to assist in positioning and rotation of the lower yoke portion.

For ease of illustration, FIG. 2A demonstrates pivoting of the screw shank 25 with respect to a stationary yoke device 15. However, if screw shank 25 is disposed in a surface of a vertebra, the yoke device 15 will actually pivot with respect to the stationary screw shank 25. The lower yoke member 17 is rotated clockwise (when viewed from above) in direction B so that slot 71 and a plane of pivoting of the pedicle screw 12 are no longer aligned with the axis of the spinal rod 16. At any rotational position of the lower yoke member 17 the screw shank 25 may be pivoted forward in direction C to a number of positions. The screw position 81 of FIG. 2A represents a neutral or straight position where the screw shank 25 is aligned along the axis 55 of the yoke device 15. As the screw shank 25 is pivoted forward in direction C, the screw shank may reach position 82 and eventually position 83. Similar positions are available when the lower yoke member 17 is rotated to various other orientations with respect to the upper yoke member 16.

FIG. 2B demonstrates counterclockwise rotation of the lower yoke member 17 in direction D opposite that of direction B. When compared to FIG. 2A, this direction of rotation allows the pedicle screw shank 25 to pivot forward in a different direction, allowing the screw shank 25 to pivot in a direction E to positions 84, 85, and other angles along the same plane. It should be noted that direction E represents a forward pivoting of pedicle screw 25 just as direction C in FIG. 2A. However, since lower yoke member 17 has been rotated to a different orientation, direction E is denoted with a separate identifier.

In order to assemble the yoke upper and lower members together, either the lower yoke member 17 or upper yoke member 16 may be provided with resiliently deflectable portions configured for one-way insertion into the other member. For instance, flanges 67 of the upper yoke member 16 may be resiliently deflectable tabs that snap-lock into a groove 77 of a rigid lower yoke portion, as shown in the cross-sectional view of FIG. 3. The tabs or flanges 67 deflect inward as their sloped entry surfaces 67a cam against lip 78 when the upper yoke member 16 is linearly driven into contact with the lower yoke member 17, and then resiliently deflect outwardly into groove 77 once the entry surfaces 67a of the flanges 67 clear the lip 78. The lip 78 of the lower yoke member located above the annular groove retains flanges 67 within the groove 77 by abutting against retaining surfaces 67b of the tabs which have a shallow enough slope to resist camming that leads to inward deflection of the tabs. The flanges 67 are allowed to glide within groove 77, providing the rotatable coupling between lower yoke member 17 and upper yoke member 16.

Alternatively, portions of the lower yoke member may deflect inwardly or outwardly to receive the lower end of the upper yoke member, or a third yoke portion may be provided to link the upper and lower yoke members. The upper yoke portion may also be configured to receive the lower yoke portion. Any other fashion of rotatably coupling the upper yoke member to the lower yoke member may also be used.

Figure 3:
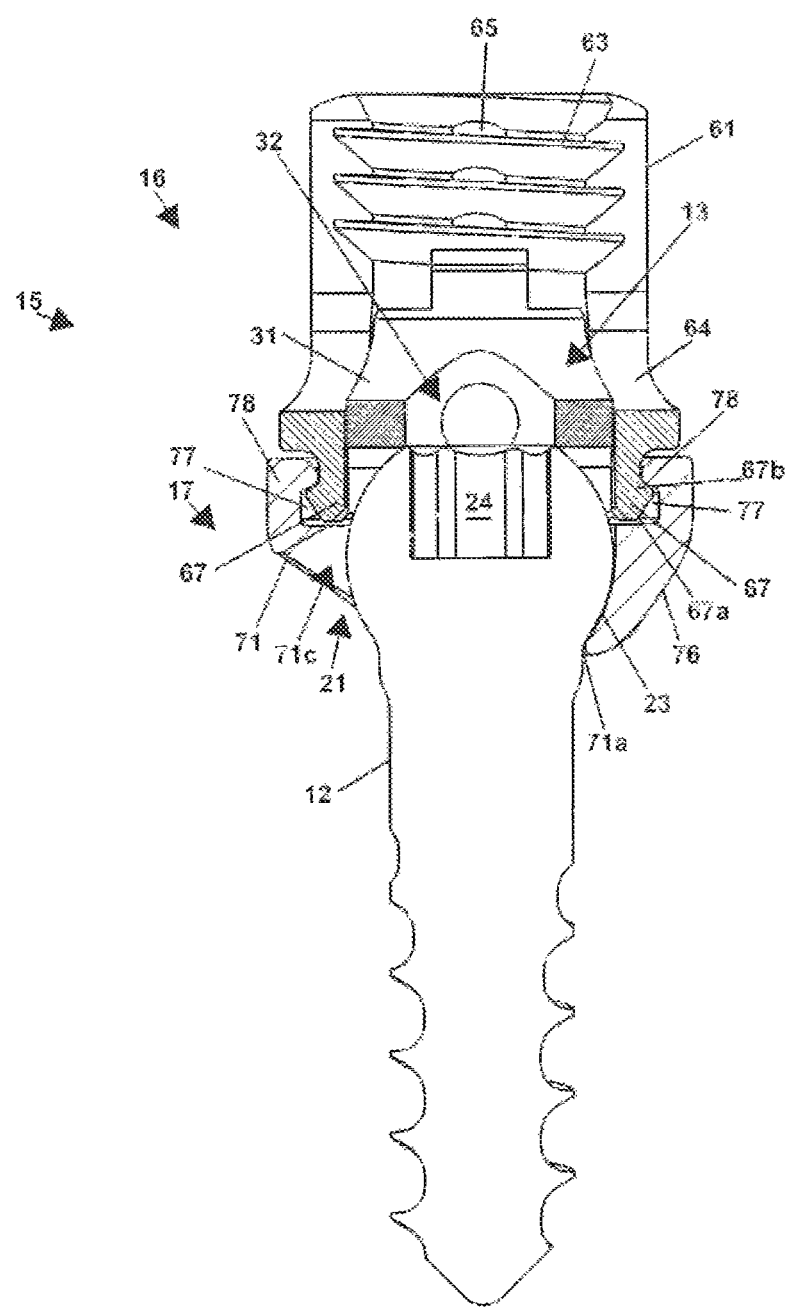
FIG. 3 is a cross-sectional view of the coupling assembly showing the rotary connection between the upper yoke member and the lower yoke member.

As illustrated in FIG. 3, an insert member 13 may also be provided in order to provide additional stability to the assembly. In the illustrated form, the insert member 13 is linearly inserted through the top of the upper yoke member 16 after the upper yoke portion 16 and the lower yoke portion 17 have been rotatably coupled. The illustrated insert member 13 inhibits decoupling of the upper and lower yoke members by occupying the space at the center of the yoke device and preventing inward deflection of coupling flanges or tabs 67. Once insert member 13 is disposed within the interior of the upper yoke member 16, the sides of the insert member abut inner surfaces of the coupling tabs 67, maintaining the position of the tabs in the groove 77 of the lower yoke member 17.

In the illustrated form, a passage 32 is provided through insert number 13 to allow access to the tool recess 24 of the pedicle screw 12 even when insert member 13 is located within the yoke. An upper surface 31 of insert member 13 is configured to be positioned flush with the exterior surface of a spinal rod. Although not a necessary feature, the illustrated form shows the upper surface 31 of the insert 13 having a contour matching the cylindrical surface of the spinal rod. When the spinal rod is inserted into the construct, it will rest upon seating surfaces 64 of the upper yoke and/or the insert seating surface 31.

FIG. 3 also illustrates how the lower yoke member 17 favors pivotability of the pedicle screw 12 in a particular direction and is constructed to retain the screw against high loads. From this cross-sectional view, it can be seen that the slot opening 71 extends from the bottom of the lower yoke member 17 (allowing the screw 12 to extend into a straight or neutral position) to only one side of the lower yoke portion (to the left in FIG. 3) allowing the screw to pivot to a predetermined maximum angle away from the neutral position, such as 60 degrees. The positioning of the screw is limited by the ends 71a and 71b of the slot opening 71.

While the shape and orientation of the anchor opening 71 permits the pedicle screw 12 to pivot to a more extreme angle than would be allowed by an opening centered at the bottom of lower yoke member 17, the distance from the first end 71a of anchor opening 71 to a second end 71b of anchor opening 71 may be comparable to the diameter of the anchor opening in most prior art multiaxial screws having symmetrical pivotability about an axis of the coupling device. However, the opening 71 can be substantially narrower in width, since the screw only needs to pivot along one plane. It can be seen in FIG. 3 that a rear wall 76 of the lower yoke member that is opposite the opening 71 contacts a substantial amount of the lower surface 23 of the pedicle screw head 21. This serves to increase the holding strength of the yoke device, preventing forces applied to the assembly from within the body from deforming the lower yoke member 17 and pulling the pedicle screw 12 out of the yoke device 15 through the slot opening 71.

As indicated above, retention features may be disposed on the upwardly directed yoke arms 61 to receive and secure a locking cap member. In one form, such retention features may be threads 63 configured to mate with opposing threads located on a locking cap member, although other configurations may alternatively be used. In the illustrated form, a notch 65 traverses the thread pattern to allow alignment wings of the insert member 13 to pass as the insert member is linearly inserted through an upper opening of upper yoke member 16 without rotation. The insert member may alternatively be designed to be inserted in another manner.

Figure 4:
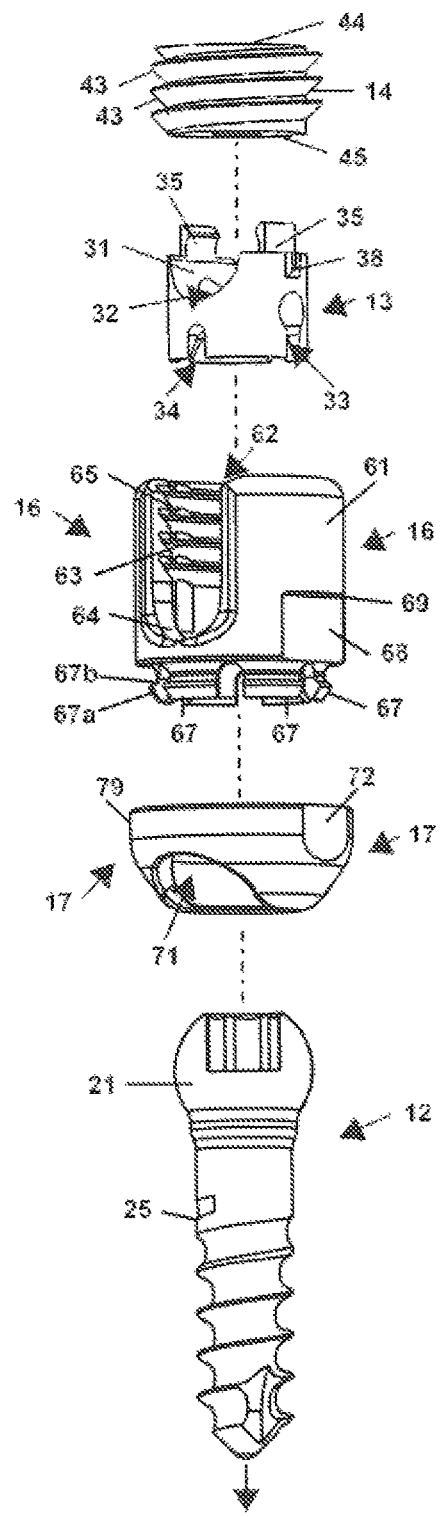
FIG. 4 is an exploded view of the coupling assembly of FIGS. 1-3 showing the anchor member and upper and lower yoke members along with an insert member and a cap member for being received in the connected upper and lower yoke members.

FIG. 4 is an exploded view illustrating the components of the coupling device and a pedicle screw anchor member 12, with all of the components aligned along the primary axis 55 of the coupling device. The illustrated components are assembled along axis 55 to couple the pedicle screw 12 to a spinal rod. In order to assemble the components, the screw 12 is inserted through the top of the lower yoke member 17 so that the shank 25 of the screw 12 extends through the elongate opening 71 in lower yoke member 17 but the head portion 21 of the screw 12 is retained within the lower yoke member. Upper yoke member 16 is then driven axially into the lower yoke member 17 so that resiliently deflectable tabs 67 snap-lock into the lower yoke member 17, providing a rotatable coupling between yoke members 16 and 17. Insert member 13 is then axially inserted through the top of the upper yoke member 16 between the arms 61 thereof. If desired, the upper yoke member, lower yoke member, screw, and even the insert member may be provided in a pre-assembled state for use by a surgeon.

When the insert member 13 is disposed within the yoke device, and the spinal rod positioned adjacent the upper concave surface 32 of the insert member, the locking cap member 14 may be used to secure the positioning of the spinal rod. In the illustrated form, locking cap member 14 is provided with threads 43 complementary to the threads 63 of the yoke device. Locking cap member 14 is rotationally inserted between the arms 61 of the upper yoke portion 16. As the cap is rotated, it is driven downward into contact with the rod, applying a locking force downward parallel to yoke axis 55. A recess 44 or other manipulation feature may be provided on the locking cap in order to assist in engagement of an instrument and rotational insertion of the cap member.

It should be noted that cap member 14 need not be a set screw as illustrated in FIG. 4. Instead, the cap member may be fitted with discrete flanges, or may be designed to be linearly inserted either along axis 55 or transverse to axis 55. For instance, a locking cap may be provided that snap-locks within upper yoke member 16, similar to the locking device described and illustrated in U.S. Patent Publication No. 2008/0045955, which is hereby fully incorporated herein. Other cap structures may also be adapted for use in the present system, including but not limited to the locking devices disclosed in U.S. Patent Publication 2009/0030457, which application is also fully incorporated by reference as if fully set forth herein. A locking cap that mates with external features of the yoke device may also be used alone or in combination with other styles of locking caps. Other cap structures may also be adapted for use in the present system, including but not limited to the locking devices disclosed in U.S. Patent Publication 2009/0030457, which is hereby also fully incorporated herein by reference.

Figure 5C:
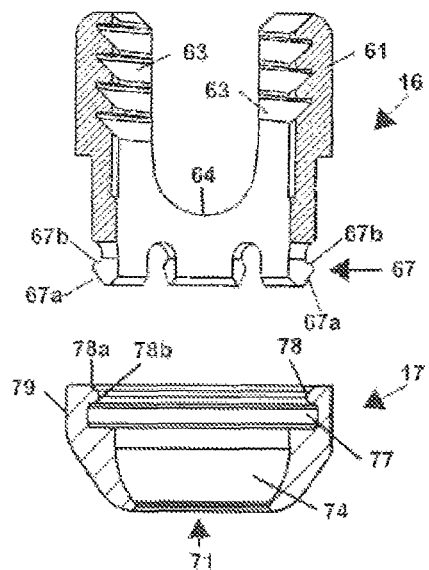

Details of the upper and lower yoke members are further illustrated in FIGS. 5A-5D. FIG. 5A shows the upper and lower yoke members from a perspective slightly below the two members. As described previously, upper yoke member 16 has upright arms 61 that form a channel 62 through which the spinal rod is received. The surface between upright arms 61 may be configured as a seat 64 contoured to support the exterior surface of a spinal rod. The seat surface 64 need not necessarily match the contour of the spinal rod, and in fact need not even come into contact with the spinal rod when it is locked in place within the yoke device. The interior surfaces of yoke arms 61 contain threads 63 or other features to secure a locking cap member. In the illustrated form, notches 65 interrupt the threads to allow alignment features of an insert portion to pass therethrough. Resiliently deflectable flanges 67 are located on the bottom of the upper yoke portion 16. An axial passage 98 extends through upper yoke portion 16, allowing an anchor member, instruments, and other devices to pass through upper yoke member 17 from the top to the lower yoke member 17 when yoke members are assembled. Exterior features, such as flat surfaces 68 and shoulder regions 69, may be provided on the upper yoke member in order to provide engagement surfaces for instruments and assist in manipulation of the upper yoke member.

The lower yoke member 17 is configured to have a profile that interferes minimally with other device structures as well as tissues in the body. To that end, side and rear walls 75 and 76 of the lower yoke member 17 may be tapered or spherical to reduce overall bulk of the yoke assembly. Through the elongate slot opening 71 an interior surface 73 may be seen. Interior surface 73 is contoured to receive the head portion of an anchor member, such as a pedicle screw, and contact a significant portion of the surface thereof. For instance, the lower yoke interior surface may be generally spherical with a radius of curvature that matches the curvature of the anchor head, surrounding the anchor head on three sides.

External yoke features may be provided to assist in manipulation (e.g., rotation) of the lower yoke member. For instance, a flat surface 72 on one side of the lower yoke member is designed to interact with an instrument for rotation of lower yoke member 17, as will be described further herein. This flat surface ensures that the lower yoke member 17 will be received by the instrument in only one orientation.

The same structures of the upper and lower yoke members 16 and 17 can be seen in perspective from slightly above the disassembled yoke device in FIG. 5B. In this perspective, the annular groove 77 in which coupling flanges 67 are received can be seen. Once the coupling flanges 67 are disposed in the groove 77, the lower yoke member 17 may be freely rotated like a turret with respect to upper yoke member 16. A cross-sectional view of the upper and lower yoke portions is shown in 5C. Once again, the annular groove 77 of lower yoke member 17 is shown. When upper yoke member 16 is driven linearly into the top of lower yoke member 17, inwardly tapered entry or guide surfaces 67a of the coupling flanges 67 will abut inwardly sloping guide surfaces 78a of the lip structure 78 located directly above the annular groove 77. Sliding of guide surfaces 67a against the guide surface 78a of the lower yoke member will cause inward deflection of resilient coupling tabs 67. Once guide surfaces 67a have cleared the guide surface 78a, the coupling flanges 67 will resiliently deflect outward into the annular recess 77. Upper retaining surfaces 67b of the coupling flanges 67 have a slope that is shallow enough that abutment against lower surface 78b of the lip structure 78 resulting from pulling upward on the upper yoke member does not cause inward deflection of coupling flanges 67 once the flanges are disposed in the annular groove 77. In this manner, the upper yoke member 16 resists disassembly from lower yoke member 17 once snap-locked into position. If desired, however, a release mechanism may be provided to deflect coupling flanges 67 inward to facilitate disassembly of the upper and lower yoke portions.

Figure 5D:
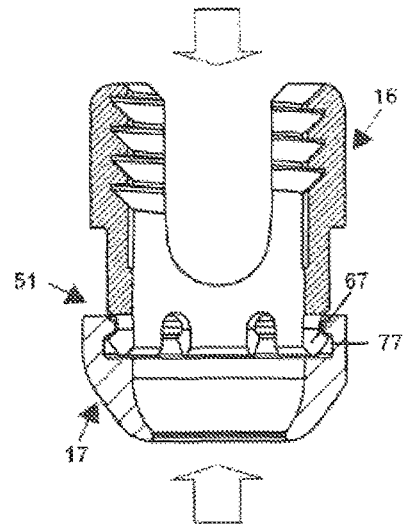

FIG. 5D shows the upper and lower yoke portions once assembled. Arrows indicate forces applied to the two structures in order to snap-lock them together into a rotatable coupling. The upper and lower yoke rotate at a coupling interface or junction 51 created by the tongue and groove connection formed by the coupling flanges 67 and the annular groove 77.

Figure 6A:
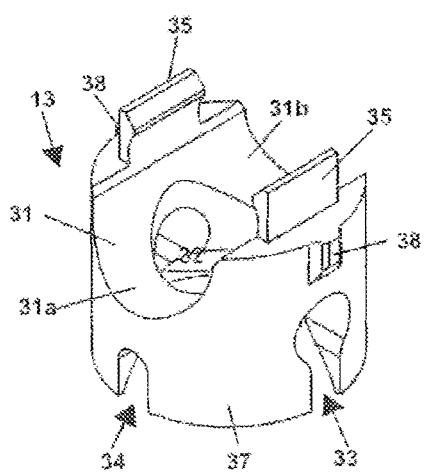
FIGS. 6A and 6B are perspective views of an exemplary insert core member from the top and bottom, respectively.
Figure 6B:
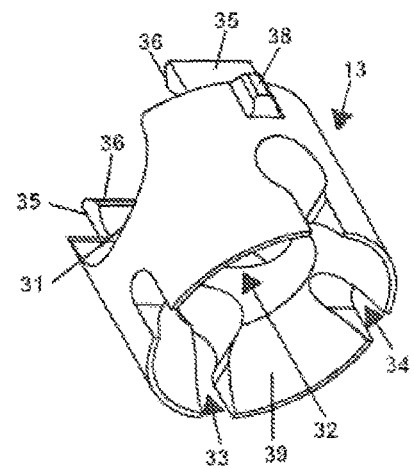

The insert member 13 that fits inside the yoke device between the anchor and spinal rod is provided with an upper concave surface for seating the spinal rod and a lower surface contoured to mate with the head portion 21 of the pedicle screw 12 as shown in FIGS. 6A and 6B. FIG. 6A is a perspective view from above the optional insert member. As previously noted, the illustrated insert member 13 is generally cylindrical in shape. The upper surface will abut a spinal rod received in the yoke device, and therefore may be contoured with a concave cylindrical surface in order to mate with the spinal rod. It has been discovered that providing an opening 32 within the insert member provides increased grip force on the spinal rod by providing contact with the spinal rod at spaced apart surfaces 31a and 31b rather than continuously across upper surface 31 of the insert 13. The passage 32 running axially through the insert member also allows a screw driver or other tool to pass therethrough and interact with the tool recess of the anchor head.

Slits 33 and 34 allow the insert member 13 to splay when forced into contact with the head 21 of pedicle screw 12, providing maximum friction between the insert member and screw head and also abutting and resilient tabs 67 of the upper yoke member, forcing the tabs outward to ensure secure coupling of yoke portions 16 and 17. In the illustrated embodiment, slits 34 aligned with the upper seating surface 31 are shorter in length than slits 33 along the sides of the insert in order to maintain a minimum wall thickness around the perimeter of the insert member. Slits 33 are enlarged to optimize the insert member's ability to splay. However, if desired all of the slits may be of a uniform size, or may be greater or less in number than illustrated in FIG. 6. In fact, no slits need be provided, and a rigid insert with no ability to splay outward may be provided. Alternatively, insert member 13 may be made from a deformable material so that its lower surface may conform to the shape of the head of the anchor member without having any slits in its side wall.

The insert member 13 may also include optional tabs 35 to provisionally secure the spinal rod. Tabs 35 are designed to resiliently deflect outwardly as the spinal rod is shifted into the upper surface 31 of the insert member 13. As the spinal rod is seated in the upper contoured surface 32, tabs 35 shift inwardly to mate to the contours of the upper surface of the rod. Insert member may also optionally be designed to include alignment features such as wings 38. The alignment wings 38 passed through grooves or notches 65 in the upper yoke member 16 as the insert member 13 is axially inserted into the upper yoke member 16 from the top. This maintains the orientation of insert member 13 as it is inserted, ensuring that the concave cylindrical surface 32 at the top of the insert member is aligned with seating surfaces 64 in channel 62 of the upper yoke member 16.

FIG. 6B is a perspective view from below the insert member 13 of FIG. 6A. Lower surface 39 of the insert member may be semi-spherical in order to provide a relatively large area of contact with the head portion of the anchor member. However, the lower surface of the insert member may be of any shape provided that force exerted downward upon the insert member is capable of applying sufficient downward force and friction to the head of the anchor member to lock the anchor member in a desired angular relationship with respect to the yoke device. It has been discovered that contouring lower surface 39 of the insert member to be of a semi-spherical shape with the same radius of curvature as the head of the anchor member advantageously increases the area of contact between the insert member and the anchor head applying a greater amount of friction to maintain positioning of the anchor head in comparison to mismatched surfaces. However, if desired, the lower surface may be contoured to be a spherical or semi-spherical surface with a radius of curvature different than that of the anchor head. For instance, the insert member lower surface may have a radius of curvature smaller than the radius of curvature of the anchor head, so that forcing the insert member into contact with the anchor head causes additional splaying of the insert member side walls. Additionally, as noted above, the lower surface of the insert member may have various other shapes and configurations.

Assembly and implantation of a coupling device is demonstrated in FIGS. 7A through 7F. The upper yoke member 16, lower yoke member 17, and insert member 13 may be provided as a preassembled construct ready for the surgeon to implant. Alternatively, the parts may be provided in unassembled state awaiting assembly during surgery. However, if the parts are provided in a disassembled state, preferably instrumentation will be provided to snap-lock the upper yoke member 16 within the lower yoke member 17, since the parts will be preferably configured so that a significant amount of axial force is required to force coupling tabs 67 into the lower yoke member, ensuring that the upper yoke member 16 will not become easily separated from the lower yoke member 17.

Figures 7A, 7B, 7C:
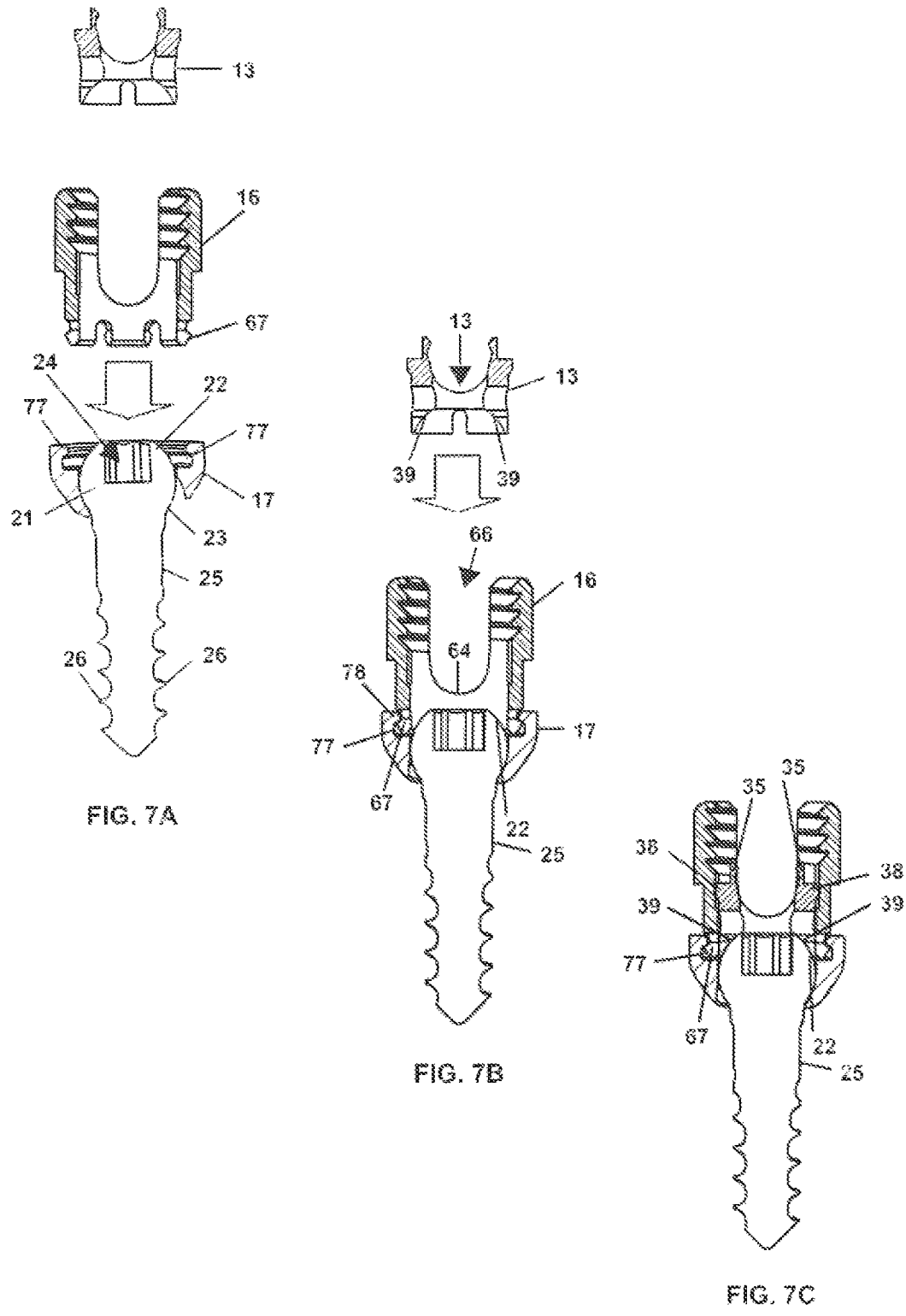
FIGS. 7A-7H show the steps for sequential assembly and implantation of the coupling assembly.

If the parts are provided separately, implantation begins as in FIG. 7A. The anchor member, in this case a pedicle screw, is seated within the cup-shaped lower yoke member 17 with the shank portion 25 extending through the slot opening in the lower yoke member. The anchor member 12 may be secured to the spine at this stage, if desired. In this case, an instrument is placed in tool recess 24 to allow the manipulation of the anchor member 12 in order to attach the anchor member to the spine. As the anchor member is rotated in a predetermined direction, the shank 25 will be screwed into the bony surface of a vertebra. The upper and lower yoke members are then rotatably coupled to one another by shifting the upper yoke member 16 along its axis into contact with the lower yoke member 17, as seen in FIG. 7B. Upward force is applied on lower yoke member 17 while downward force is applied on upper yoke member 16 so that coupling tabs 67 are forced into the interior of lower yoke members 17, eventually resulting in the placement of coupling tabs 67 in the annular groove 77 of the lower yoke member.

It may be desired to provide adequate space between the annular groove 77 and the upper surface of the anchor head 22 to allow inward deflection of coupling tabs 67 sufficient to clear the surface of the lip portion 78 at the top of the lower yoke member. The tabs 67 or other portions of the upper yoke member may optionally be sized and configured to prevent the screw head 21 from exiting upward out of the lower yoke member. Alternatively, the yoke members may be sized and configured for coupling only prior to loading of the anchor member into the yoke device. Once coupling tabs 67 are disposed in annular groove 77, upper yoke member 16 may freely rotate with respect to lower yoke member 17.

The step of assembling the upper and lower yoke members may alternatively be accomplished by the surgeon prior to inserting the anchor member 12 into bone, or as previously mentioned, may take place at the point of production to provide a preassembled yoke device. In either of these cases, an instrument such as a screw driver is inserted through the axial passage of the upper yoke member 16 into tool recess 24 in order to manipulate the anchor member 12 and attach it to the spine.

Once the upper and lower yoke members are assembled, and the anchor member disposed therein, the optional insert member 13 is inserted into the passage 66 of the upper yoke member along the yoke's axis. This step may also be accomplished prior to attachment of the anchor member 12 to the spine. However, if the insert member 13 is provided in a preassembled state with the yoke device 15, it is recommended that the insert member 13 be only partially inserted into the yoke device 15 so that friction between lower surface 39 of the insert member and upper surface 22 of the anchor head does not make it difficult to manipulate anchor member 12 and secure the anchor member to the spine. An axial passage 32 may be provided in the insert member in order to allow an instrument to access tool recess in the anchor member after introduction of the insert member into the yoke device.

The insert member 13 may be sized and configured to retain its position within the yoke device once inserted. For instance, the alignment wings 38 on the sides of the insert member may be configured for one-way locking against the interior of the yoke device, such as by snap locking within grooves or other detents of the upper yoke member. Once the insert member is fully inserted into the yoke device, as in FIG. 7C, frictional forces provisionally hold the anchor member 12 at a selected orientation with respect to the yoke device. These frictional forces also provisionally hold the upper yoke member 16 at a selected rotational position with respect to lower yoke member 17 because of frictional forces between the anchor head and insert member combined with structural features such as alignment wings 38 of the insert member that maintain a fixed orientation between the insert member and the upper yoke member 16. These frictional forces may be overcome in order to adjust the yoke device prior to final locking, but are preferably strong enough to avoid accidental tilting and/or rotation of the yoke members.

Figures 7D, 7E:
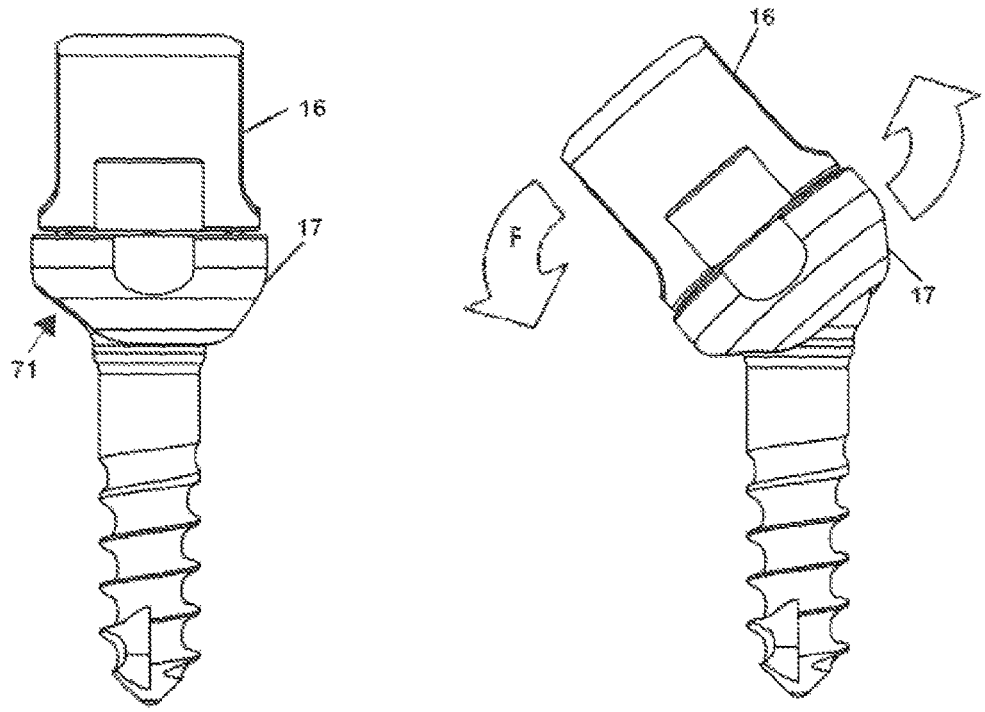
Figure 7F:
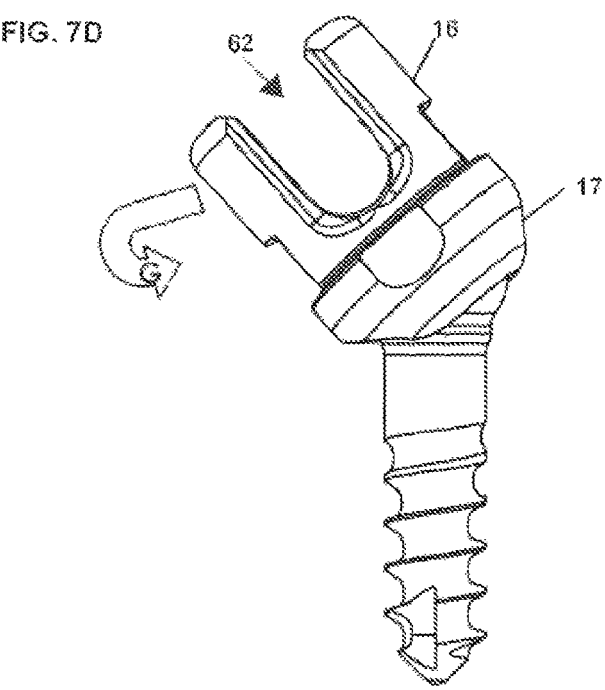

After the upper yoke member, lower yoke member, insert member, and anchor member have been provisionally assembled, the yoke device provides a polyaxial coupling relationship between the anchor member 12 and the spinal rod or other elongate member 18. FIGS. 7D through 7F demonstrate the tilting and rotation of a yoke device in order to accommodate the positioning of a spinal rod that is offset with respect to the axis of the anchor member. In FIG. 7D, a yoke device 15 is shown secured to the spine and in an upright neutral position with respect to the anchor member 12. The slot opening 71 of the lower yoke member 17 may be rotated into position so that it faces the direction in which the yoke device is to be tilted. Applying force to the yoke device 15 along a plane running through opening 71 in the lower yoke member 17 will cause pivoting or tilting of the yoke device in direction F, as shown in FIG. 7E. When a desired angular relationship between the anchor member and yoke device is achieved, the yoke device is released and frictional forces between the screw head, insert member, and yoke device provisionally maintain the selected orientation. Rotational force is applied to the upper yoke member 16 in order to overcome the frictional forces and align the channel 62 of the upper yoke member in a desired direction to receive a spinal rod. FIG. 7F shows the upper yoke member rotated in direction G with respect to the lower yoke member for receiving a spinal rod. Of course, the upper yoke member may also be rotated prior to pivoting or tilting of the yoke device.

As previously noted, rotational force may be applied to the lower yoke member 17 relative to the anchor member in order to orient the opening 71 in a desired direction of tilting. In this manner, the yoke device may be tilted in any direction around the anchor member prior to aligning the upper yoke member so that its channel is oriented to receive a spinal rod.

Figure 7G:
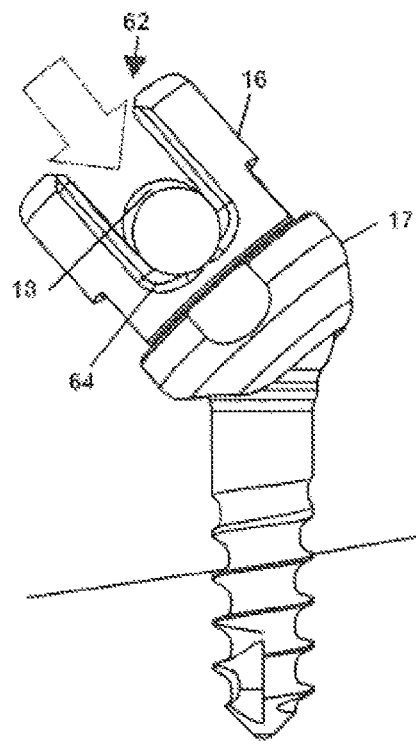

After the spinal rod is received in the channel of the upper yoke member, force is applied on the spinal rod in order to shift the rod into the yoke channel 62 and against the seating portion 64 of the upper yoke member and/or the seat of the insert member as shown in FIG. 7G. The application of force onto the spinal rod in turn shifts the insert member 13 into tight contact with the anchor member head, pressing the anchor head against the interior of the lower yoke member and providing sufficient friction to fully lock the position of the lower yoke member and upper yoke member with respect to the anchor head. If an insert member is not provided, the device should be designed so that friction between the rod itself and the anchor member head is sufficient to lock the positions of the upper yoke member and lower yoke member.

Figure 7H:
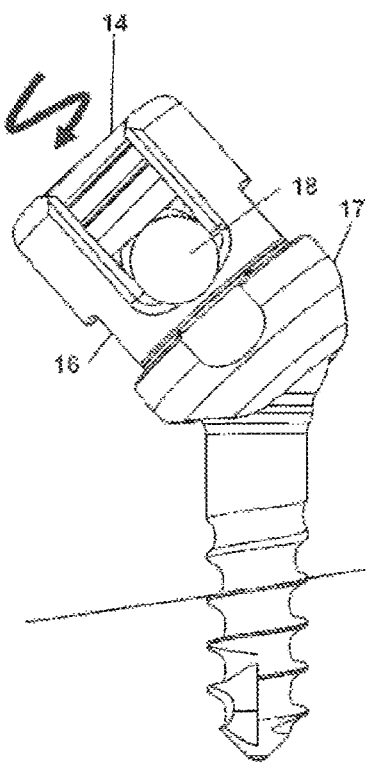

Rotation of the insert member will be resisted not only by friction between the rod, insert member, and anchor member, but also optionally by alignment wings disposed in vertical grooves of the yoke device and by the contours of the upper insert surface which maintains alignment of the insert member with respect to the spinal rod. The spinal rod is secured within the channel 62 of the yoke device with a locking cap member 14 as shown in FIG. 7H. The locking cap 14 may be disposed in the yoke device after reducing the rod and full seating thereof in the yoke device, or may be designed to impart the very forces responsible for shift the spinal rod into the fully seated position. Tightening the locking cap maintains the frictional forces between the components that hold the spinal rod and anchor member in a fixed orientation.

The locking cap member 14 may be of any configuration, but should be designed to exert a force along the primary axis of the yoke device sufficient to maintain the spinal rod in position and maintain forces that apply friction between the spinal rod and the insert member, as well as forces between the insert member, anchor member, and yoke device so that the relative positions of the anchor member, yoke device, insert member, and spinal rod do not shift under forces imposed upon them once the device is implanted.

Figure 8:
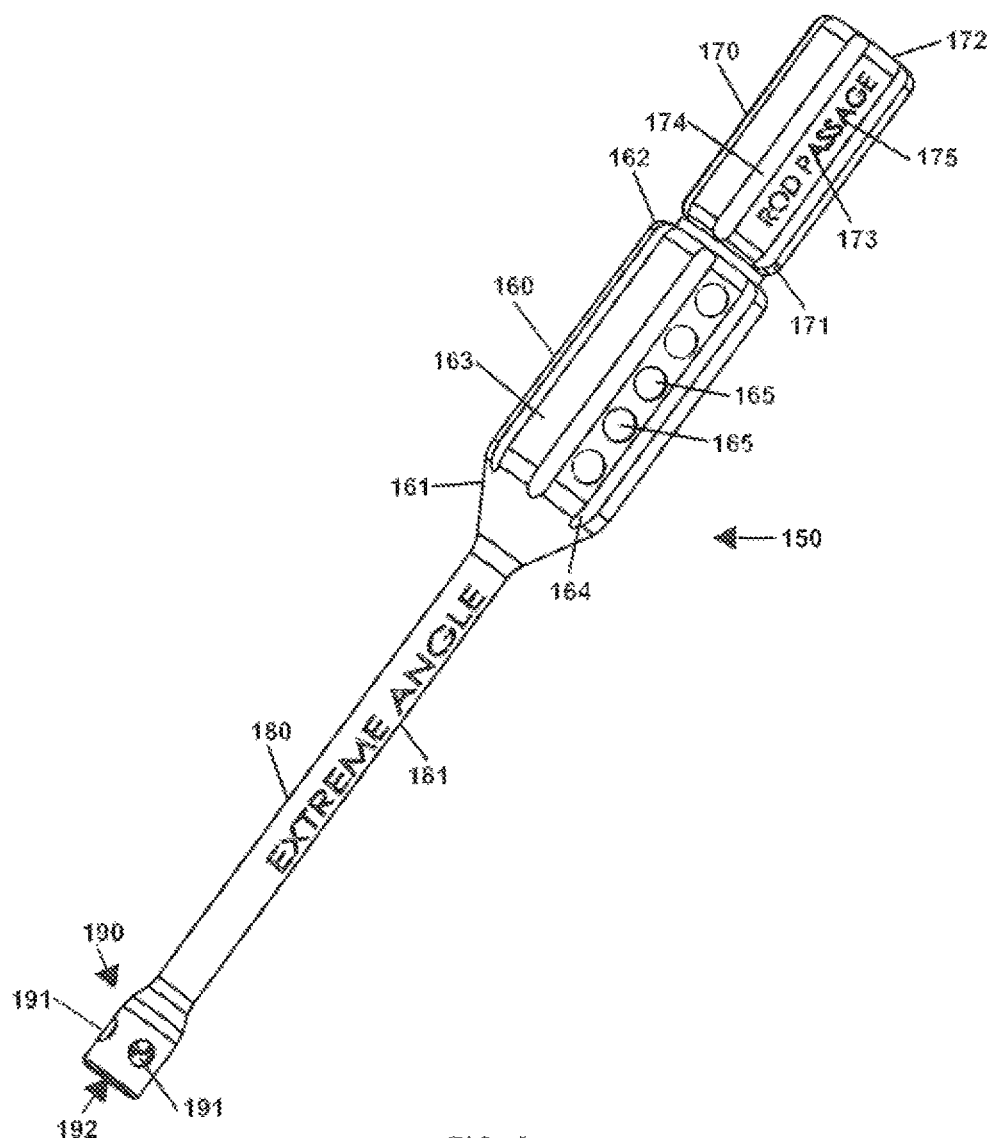
FIG. 8 is a side view of an instrument for manipulating the coupling assemblies of FIGS. 1-7.

In order to provide adjustments to the positioning of the yoke device after provisional locking of the anchor member (after the insert member is moved into place but before securing the locking member), an instrument may be provided to assist the surgeon by providing a mechanical advantage in rotating the lower yoke member, rotating the upper yoke member, tilting of the yoke device, or a combination thereof. An exemplary instrument for positioning the yoke device is shown in FIG. 8.

The exemplary instrument 150 includes a head or receiver portion 190 for receiving the yoke device, an elongate neck 180 connecting the head portion to a first handle member 160, and a second handle member 170. The head portion 190 includes a cavity 192 for receiving the yoke device. A channel positioner 193 is disposed within the cavity 192 so that it may be located within the channel of the upper yoke member when the yoke device is received in the cavity 192. Control of the channel positioner 193 is then capable of adjusting the positioning of the channel in the upper yoke member. For instance, the channel positioner 193 may have a width similar to that of a spinal rod so that once located within the channel of the upper yoke member rotation of the channel positioner rotates the upper yoke member to align the yoke member channel in a desired direction. A bore runs through the first handle 160 and elongate neck 180, allowing the elongate channel positioner 193 located within hollow head portion 190 to be physically connected to the second handle 170 by an elongate shaft.

The first handle 160 has a first end 161 fixed to the neck portion 180, and a second end 162 opposite the first end. A grip may be provided along the outer surface 163 of the first handle for better manipulation of the instrument. For instance, grooves 164 may be placed lengthwise along the outer surface 163 of the handle spaced at intervals to provide a grip. Other features, such as circular or semi-circular indents 165 may be provided instead on the handle, or may be provided in combination with a grip for additional gripping and/or to provide a tactile indicator of the positioning and orientation of the handle.

The second handle 170 is configured in a manner similar to the first handle with a first end 171 adjacent the first handle and a second end 172 at the proximal end of the instrument. Grooves 174 or other surface features may provide grip along the outer surface 173 of the second handle. In addition, indicia 175 may be provided on the outer surface of the second handle in order to indicate orientation of the handle with respect to the rest of the instrument. The indicia 175 may be raised or recessed in order to provide additional grip and/or a tactile indicator of positioning and orientation. Since the second handle 170 is linked to the channel positioner 193 through the elongate shaft 185, the indicium 175 is preferably oriented so that it indicates the orientation of the channel positioner 193, as further described herein below. As shown, the second handle 170 is marked "rod passage" on a face that points in a direction parallel to the axis of the channel positioner 193.

Figure 9:
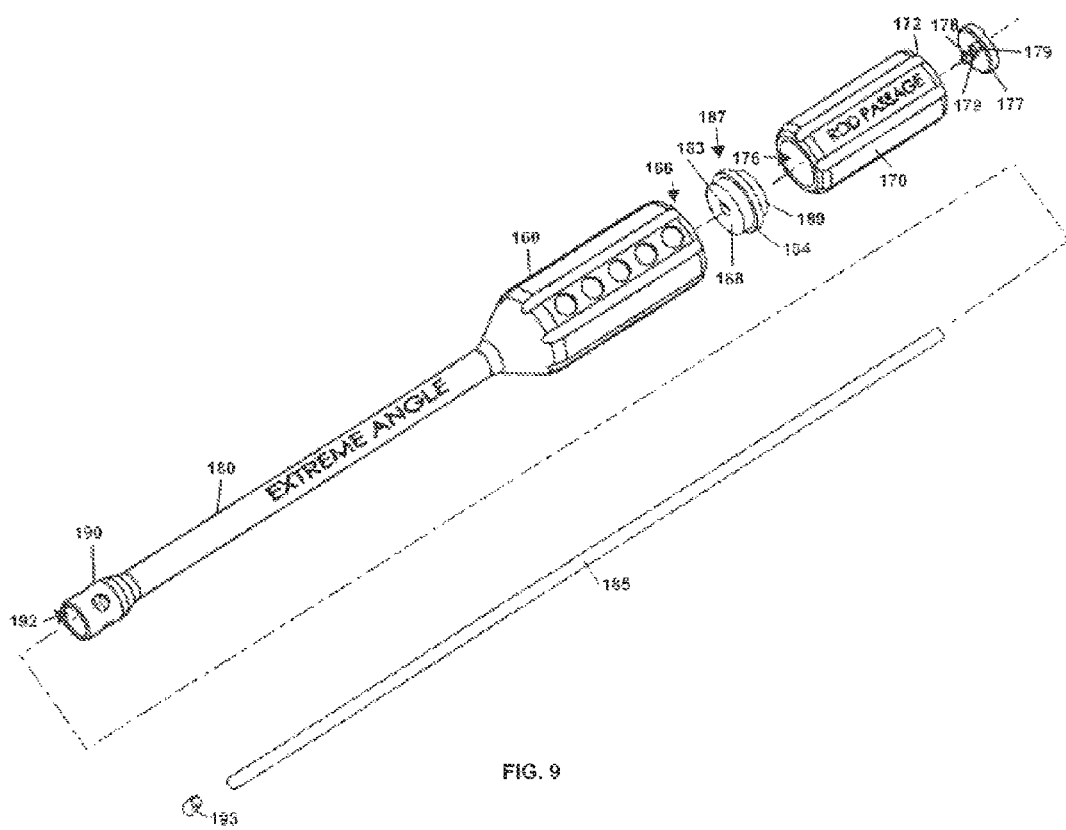
FIG. 9 is an exploded view of the instrument of FIG. 8.

In the exploded view of FIG. 9 the elongate interior shaft 185 that connects the second handle 170 with the channel positioner 193 can be seen. When the instrument is assembled, the inner shaft 185 is fixed to the channel positioner 193 at one end and to the second handle 170 at the opposite end. In the illustrated embodiment, the shaft 185 is fixed to the second handle 170 by an end cap 177 that is non-rotatably mounted to the second handle 170. The shaft 185 is disposed in an opening 178 of the end cap 177 and affixed thereto so that the shaft 185 does not rotate independent of the end cap 177. The end cap also includes one or more posts 179 or other features to fix its orientation with respect to the second handle portion 170. The end cap 177 is mounted onto proximal end 172 of the second handle 170. The manner of assembling the channel positioner 193, the shaft 185, the end cap 177, and the second handle 170 is not important, except that it should ensure that the parts do not twist, bend, or separate under amounts of torque sufficient to manipulate the yoke device.

The shaft 185 is disposed through a bore 176 in the second handle and passes through a similar bore 166 of the first handle 160. The shaft 185 also passes through a bore of the elongate neck region 180 so that the channel positioner 193 is disposed within the hollow cavity 192 of the head portion 190.

A joint member 187 may also be provided between the first and second handles in order to assist in smooth rotation between the two handle portions. The joint member 187 shown includes a central flange 184 to be disposed between the two handles, and projecting portions 189 and 188 adjacent the flange to be inserted within the bores 176 and 166 of the second handle 170 and first handle 160, respectively. An opening 183 through the joint member allows passage of inner shaft member 185. In addition to preventing direct contact of handles 160 and 170, thereby reducing friction between the two, joint member 187 also provides stability to the shaft member 185 by providing an opening 183 that receives and positions shaft member 185.

Openings 193 in the head portion 190 may be provided in order to reduce the weight of the head portion, for viewability of the channel positioner 193 located within the head 190, and to provide ease of sterilization and cleaning.

Figure 10:
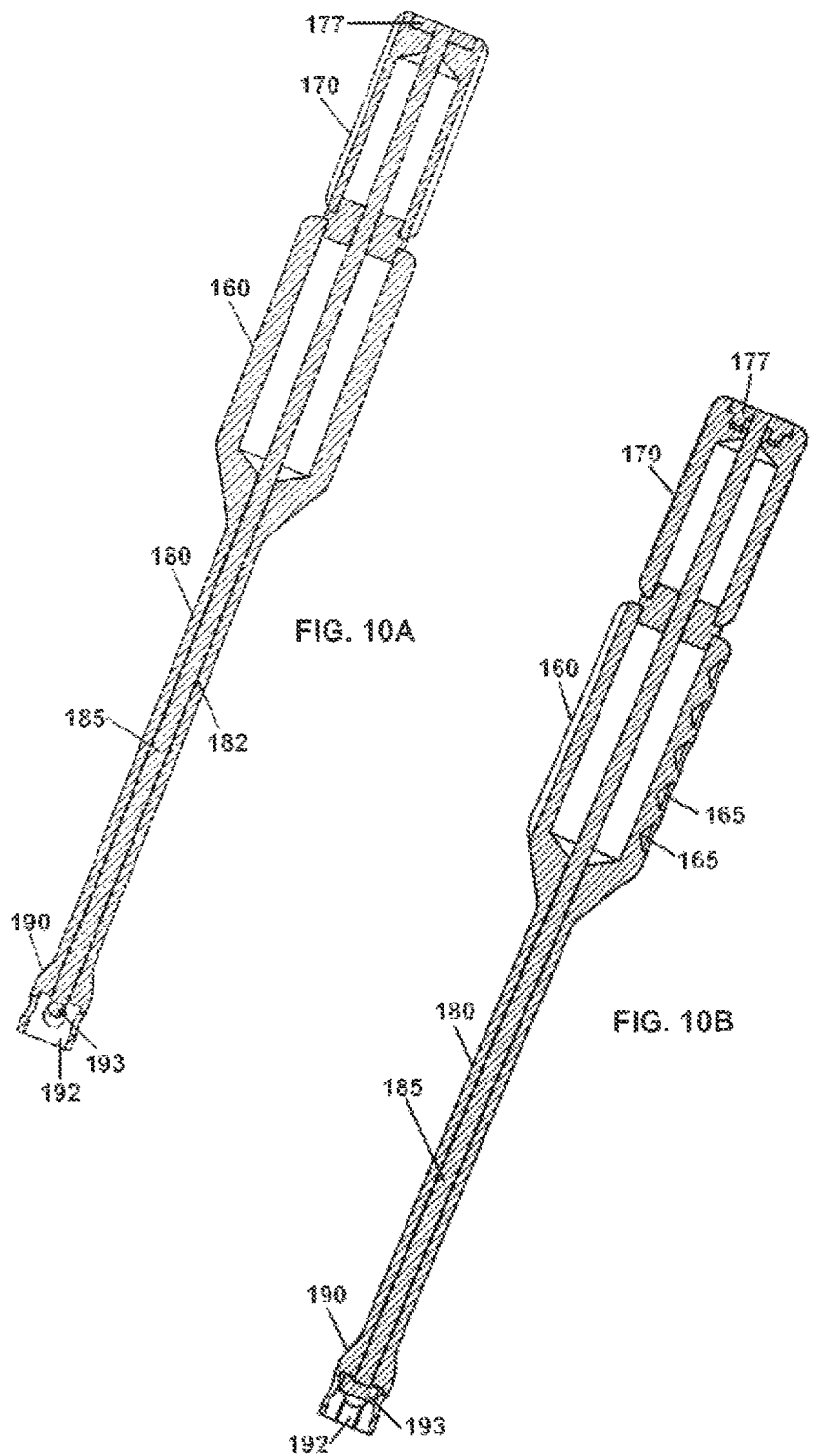
FIGS. 10A and 10B are cross-sectional views of the instrument.

The assembled instrument is shown in cross-section in FIG. 10A. Note that the neck portion 180 includes a bore 182 for passage of the inner shaft member 185. Preferably, the bore 182 is sized just large enough to accommodate the inner shaft member 185 in order to provide stability to the elongate shaft member while still permitting rotation thereof. In the cross-sectional view shown in FIG. 10A, the plane of view passes through the axis of the cylindrical channel positioner 193. The channel positioner 193 is shaped and sized to resemble a spinal rod that will be received in the channel portion of the yoke device of FIGS. 1-7. The channel positioner 193 is disposed in the hollow cavity 192 of the head portion 190. The cavity 192 is large enough to accommodate the exterior of the upper and lower yokes of the yoke device. A cross-sectional view showing the length of the cylindrical channel positioner 193 is shown in FIG. 10B. Indents 165 on the first handle 160 can also be seen from this view. Otherwise, the instrument looks much the same from this perspective as in FIG. 10A, since the instrument is relatively symmetrical about its elongate axis.

Figure 11:
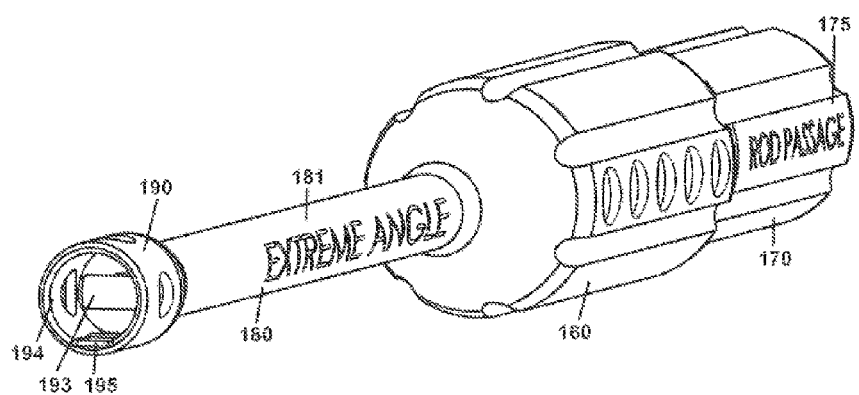
FIG. 11 is a perspective view of an instrument showing the interior of the head portion that receives a coupling device.

FIG. 11 is a perspective view showing details of the instrument head portion 190. An interior surface 194 of the head portion is relatively cylindrical in order to fit to the exterior profile of the lower yoke member 17 (see FIGS. 1-2). A positioning plate 195 deviates from this cylindrical contour, and is designed to abut the flat portion 72 of lower yoke member 17. Due to the presence of the single positioning plate 195 and the single flat surface 72 on the lower yoke member, there is only one orientation in which the lower yoke member 17 of FIG. 1 may fit into the instrument head portion 190. Therefore, when the lower yoke member 17 is received in the head portion 190 it is known that slot opening 71 for the anchor member is oriented in a specific direction. In the exemplary instrument, the direction of slot opening 71 is indicated by an indicium 180 reading "extreme angle." Of course, other indicia may be used to indicate orientation of the slot opening 71, and these indicia may be positioned on other parts of the instrument.

Since the asymmetric interior surface 194 of the head portion 190 orients the exterior surface of the lower yoke member held within, rotation of the first handle 160 which is integral with or affixed to the neck 180 and head portion 190 will result in rotation of the lower yoke member with respect to its anchor member once the anchor member is fixed into position. This allows rotation of handle 160 to adjust the plane of pivoting of the yoke device by orienting the lower yoke member. Note that the lower yoke member 17 in FIG. 1 is slightly larger in diameter than the upper yoke member 16 in order to allow rotation of the first handle 160 to rotate the lower yoke member 17 without necessarily affecting the upper yoke member 16.

Similarly, the channel positioner 193 is disposed within the upper yoke member 16 in only one of two orientations. Since the channel positioner 193 is sized to imitate a spinal rod and fit between the upper arms of the upper yoke member in the channel intended to receive the spinal rod, the elongate channel positioner 193 must be aligned with the channel in order for the yoke device to properly fit into the instrument head portion 190. Due to the symmetry of the upper yoke portion, the orientation of the upper yoke member, and thus the channel 62 therein for receiving the spinal rod, is known when the yoke device is loaded in the instrument.

Rotation of the second handle rotates the channel positioner 193, and thus positions the upper yoke member 16. Since the lower yoke member 17 is being held in the instrument head portion 190 in only one orientation, rotation of the second handle 170 relative to the first handle 160 results in rotation of the upper yoke member 16 with respect to the lower yoke member 17. An indicium 175 may be provided in order to indicate orientation of the upper yoke member.

FIG. 12 demonstrates use of the instrument of FIGS. 8-11. It should be noted that the instrument 150 can only be used prior to insertion of the spinal rod and locking cap member into the yoke device. Once a yoke device 15 has been assembled and its associated anchor member implanted into the spine, the head portion 190 of the instrument 150 slides around the yoke device in the proper alignment as shown in FIG. 12A. The lower yoke member is securely held by the interior surface 194 and positioning plate 195 of the instrument head portion, and the channel positioner 193 is disposed between the arms of the yoke member rod channel. Once the instrument is properly engaged with the yoke device, the first handle 160 is rotated until its indicium 181 is oriented into the direction in which the yoke device is to be pivoted, as shown in FIG. 12B. Tilting of the entire instrument structure toward the direction in which indicium 181 faces pivots the yoke device with respect to the anchor member, as shown in FIG. 12C. The elongate structure of the instrument provides a mechanical advantage (i.e. leverage) that helps to overcome provisional locking forces that frictionally hold the yoke device in place with respect to the anchor member. Before or after the tilting of the yoke device, the second handle 170 may be rotated as in FIG. 12D so that the indicia 175 indicates that the rod channel of the upper yoke portion has been rotated into the desired orientation to receive the spinal rod.

If desired, the handles 160, 170 of the instrument may be color coded with the yoke device to indicate which portion of the coupling device they manipulate. For instance, the lower yoke member and first handle 160 may be provided with a first color (e.g., by anodization or other technique), while the upper yoke and second handle 170 are provided with a second color.

After pivoting the yoke device and aligning the channel, the instrument may then be removed from the yoke device so that the rod and locking cap member may be secured therein. The locking cap member may be of any configuration desired as long as it exerts a locking force onto the rod, which in turn exerts a locking force downward upon the anchor member head either directly or indirectly. For instance, a set screw may be used as illustrated in FIG. 4. Alternatively, the upper yoke member 16 of FIGS. 1-7 may be configured to receive and lock with other types of locking members. Various locking cap structures are shown in FIGS. 17-21, as further explained below. Depending on the structure of the locking cap member, the yoke device can be configured various ways in order to receive and retain the locking cap member. In addition to the locking cap members shown, any design may be used, such as wedge-like locking cap members inserted linearly from the side of the upper yoke member (along an insertion trajectory parallel to the axis of the spinal rod and rod channel) to provide a locking force transverse to the direction of insertion.

Figure 13:
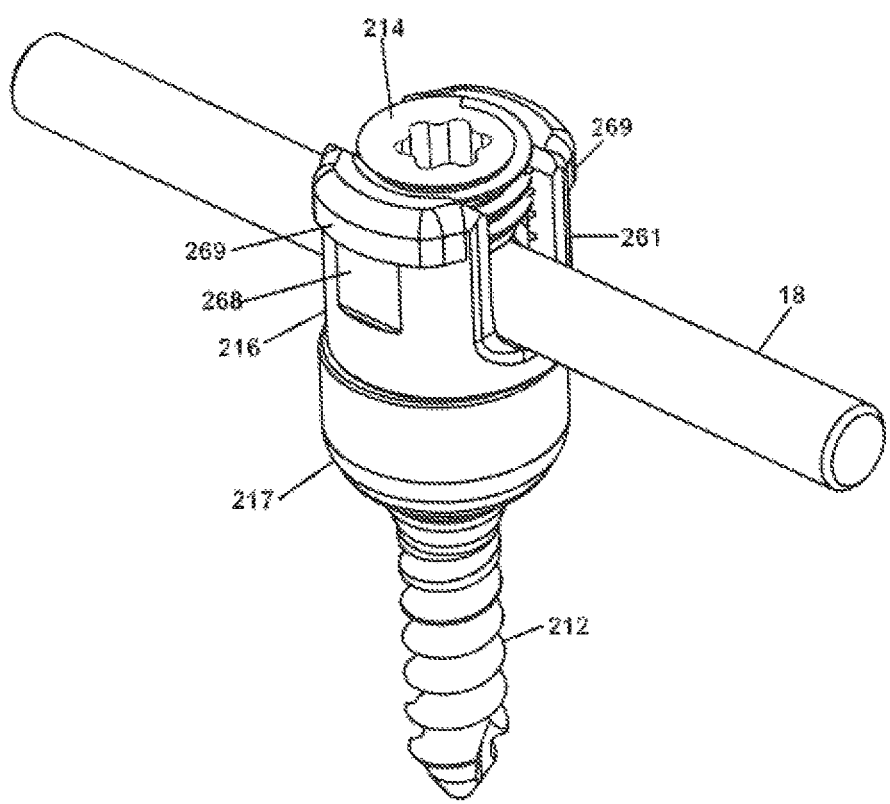
FIG. 13 is a perspective view of another embodiment of a coupling assembly.

FIG. 13 is a perspective view of another embodiment of a coupling assembly having an upper yoke member 216 that is rotatably coupled to a lower yoke member 217 for securing the position of a spinal rod 18 relative to an anchor member 212. In the illustrated form, the upper yoke member 216 of the coupling assembly has arms 261 that extend upward to form a channel for receiving the spinal rod 18 and laterally extending shoulder portions 269 for being gripped by an instrument. The flats 268 on each side of the upper yoke member below the shoulder portion 269 also aid in manipulation of the upper yoke member. A locking member 214 in the form of a set screw engages the interior surfaces of the yoke arms 261 to secure the position of the spinal rod 18.

Figure 14:
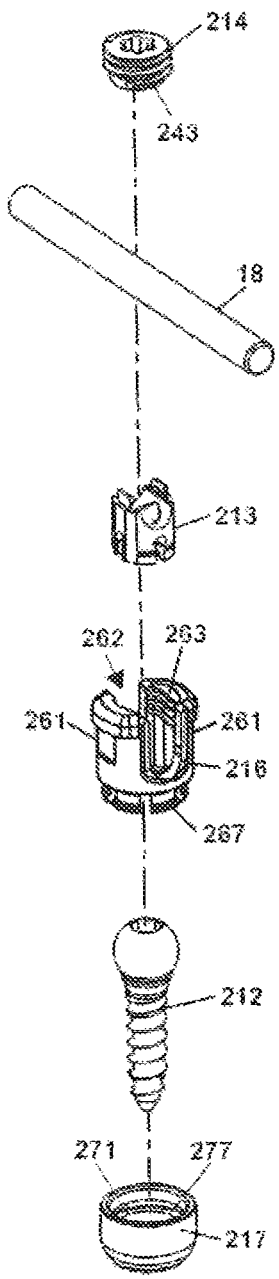
FIG. 14 is a perspective exploded view of the coupling assembly of FIG. 13.
Figure 15:
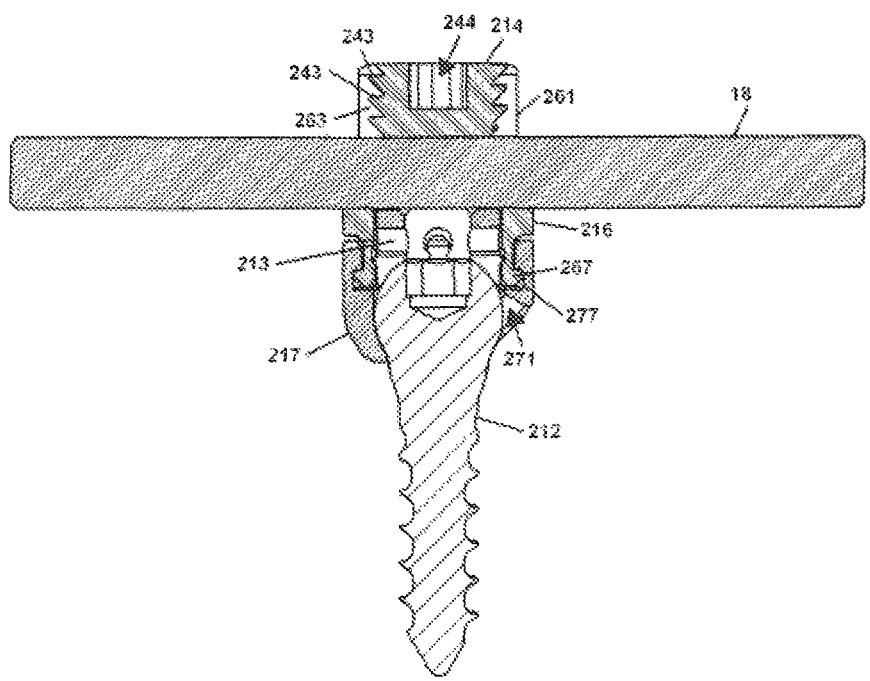
FIG. 15 is a cross-sectional view of the coupling assembly of FIG. 13.

As can be seen in the exploded view of FIG. 14, the upper yoke member 216 has resiliently flexible flanges 267 that are configured to snap-lock into an interior annular groove 277 of the cup-shaped lower yoke member 217. An off-center opening 271 is provided in the lower yoke member 217 in order to allow the anchor member 212 to pivot to one side of the lower yoke member 217 when the head thereof is received inside of the lower yoke member 217. An insert member 213 is also provided for insertion into the upper yoke member 216. The spinal rod 18 is received by the upper yoke member 216 and on top of the insert member 213. The locking member 214 is rotatably inserted between the arms 261 of the upper yoke member 216 in order to engage the threaded interior surfaces 263 and lock the spinal rod 18 within the assembly. The locking member may be, for instance, a buttress style locking screw with threads having an angled lower surface and a horizontal upper surface, a geometric configuration that resists backing out of the yoke once threaded therein. For instance, the threads of the locking member may have a pitch at their lower surface of about 45 degrees with respect to horizontal (a plane perpendicular to the axis of the generally cylindrical screw), and a pitch of zero degrees (horizontal) at their upper surface, as best shown in FIG. 15. Preferably, the thread has no lead-in portion so that the thickness of the thread is consistent throughout. Typical screws have a thread that is thin at the leading end and gradually increases in thickness. However, providing a zero-lead thread that has a consistent thickness throughout reduces the potential for cross-threading when rotatably inserting the screw into the yoke member.

The assembled device of FIGS. 13 and 14 is shown in cross-section in FIG. 15. The upper yoke member 216 is rotatably coupled to the lower yoke member 217 by positioning of the lower flanges 267 of the upper yoke member in the annular groove 277 of the lower yoke member. The anchor member 212 is received within the lower yoke member 217, and an opening 271 that extends from the bottom toward only one side of the lower yoke member allows the anchor member to pivot to a relatively extreme angle toward the spinal rod 18. Once the anchor member 212 is oriented as desired, the locking member 214 is rotatably inserted into the upper yoke member 216 so that the threads 243 of the locking member interlock with the threads 263 of the upper yoke member. A drive interface 244 of the locking member is provided to facilitate rotation and insertion. The downward force of the locking member 214 on the spinal rod 18 drives the insert member 213 in which the rod 18 is seated downward onto the head of the anchor member 212, forcing the head of the anchor member 212 against the interior of the lower yoke member 217. Friction between the anchor member, the lower yoke member 217, and the insert member 213 inhibits further pivoting of the anchor member 212. The insert member 213 also is positioned to prevent inward deflection of the flanges 267, thus maintaining their positioning in the annular groove 277 and preventing separation of the upper and lower yoke members.

Figure 16:
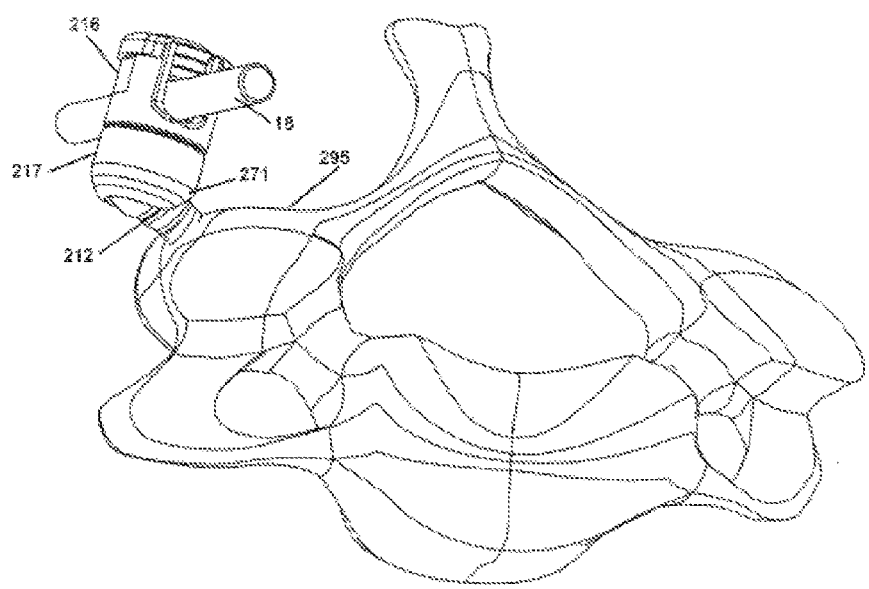
FIG. 16 is a perspective view of the coupling assembly of FIG. 13 mounted to a vertebra.

FIG. 16 illustrates the yoke device of FIGS. 13-15 mounted to a vertebra 295. As shown, the opening 271 toward one side of the lower yoke member 217 allows the yoke to be pivoted away from the axis of the anchor member 212 to a much greater degree than would be possible if the anchor opening were circular and centered at the bottom of the lower yoke member. Regardless of the degree of pivoting between the yoke and the anchor member 212, the upper yoke member 216 may be rotated to any direction relative to the lower yoke member 217 in order to receive a spinal rod 18. The versatility provided by the rotatable coupling assembly allows the upper and lower yoke members to connect anchor members and spinal rods of more varied orientations than possible with prior art devices.

FIGS. 17-21 illustrate various alternative locking members that may be adapted for use with rotatable coupling assemblies as described above. For instance, the upper yoke members of FIGS. 1 and 13 could be modified to replace the interior threading of the arm portions 61, 261 with structures configured to interlock with the alternative locking members. It will be recognized that a wide variety of other locking structures may also be adapted for use with the coupling assemblies described herein.

Figure 17:
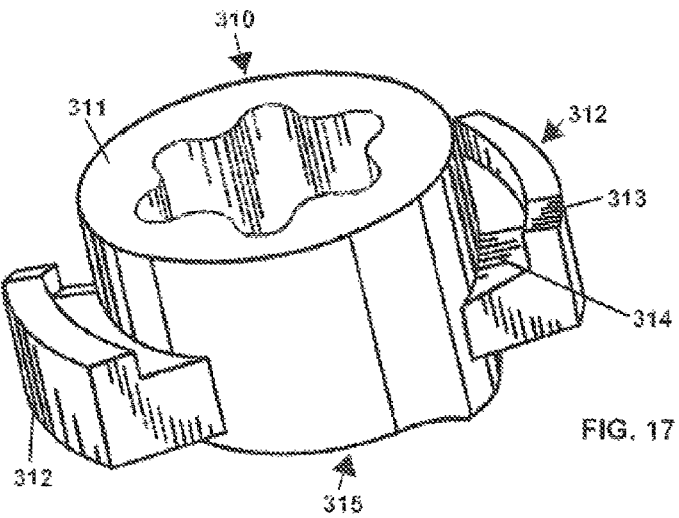
FIG. 17 is an alternative locking member with opposed flanges and a lower camming surface that may be adapted for use with the invention.

FIG. 17 shows one alternative locking member 310 having a generally cylindrical body 311 and flanges 312 located on opposite sides of the body. The upper yoke member of a coupling device would be provided with corresponding slots to receive the flanges 312 upon rotation of the locking member 310. By providing discrete flanges instead of a continuous threading, the cap member need be rotated only a fraction of a full rotation in order to lock the spinal rod in place and avoids any potential for cross-threading during insertion. The locking member also has a lower camming surface 315 contoured so that a downward force is applied upon a spinal rod as the locking member 310 is rotated. In other words, the lower camming surface 315 is contoured so that a thinner portion of the locking member 310 contacts the spinal rod when the locking member is first inserted, but a thicker portion of the cap abuts the spinal rod when the locking member is rotated to a locked position wherein the flanges 312 engage the yoke. This effectively lowers the point of contact between the locking member and the spinal rod while the flanges remain at a constant level, forcing the spinal rod downward into a fully locked position. Due to the lower camming surface 315, it is not necessary for the flanges 312 to be sloped in order to provide a downward locking force upon rotation of the locking member. However, if desired the flanges may be sloped in order to cam against the interior of the yoke member, and if so the bottom of the locking member may be configured to be relatively flat. The flanges are also provided with an upwardly directed lip 313 that extends above the upper flange surface to form a groove 314 which, when paired with slots of a yoke member having a lip that is received in the flange groove 314, resists splaying of the arms of the yoke member when the locking member 310 is rotated into place.

Figure 18A:
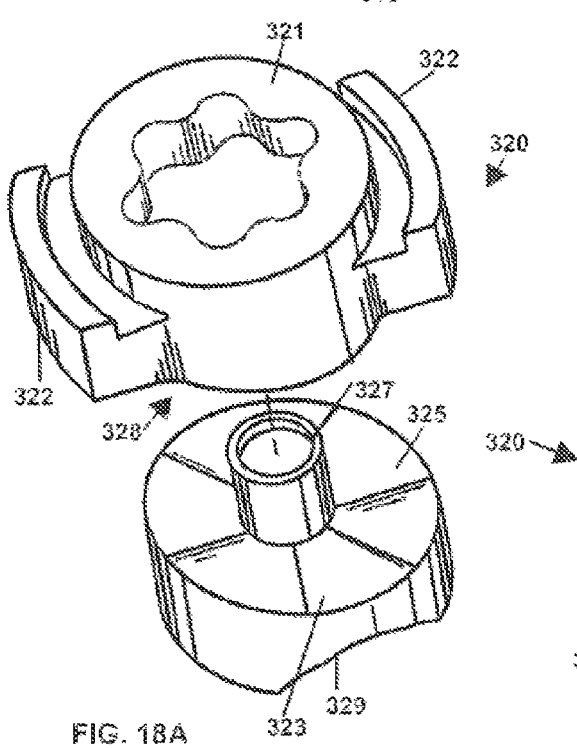
FIG. 18 is an alternative multi-part locking member with opposed flanges and a lower saddle member that may be adapted for use with the invention.
Figure 18B:
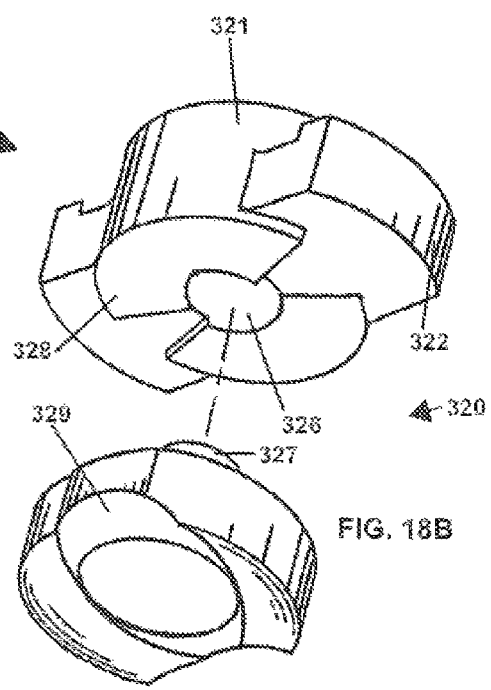

FIGS. 18A and 18B show another alternative locking member 320 that is similar to that shown in FIG. 17 but includes a saddle member 325 that maintains contact with a spinal rod as the upper cap member 321 is rotated into place. A generally cylindrical recess 329 is provided on the lower surface of the saddle member to receive the spinal rod. The upper cap member 321 has opposed flanges 322 and a lower camming surface 328 that interacts with an upper contoured camming surface 323 of the saddle member. The camming surfaces allow the saddle member 325 to be held close in one orientation but pushes the saddle member 325 away as the cap member 321 is rotated relative to the saddle member 325. A post 327 or other structure is provided to couple the cap member and saddle member, and may be provided as a separate member or as integral with either the cap member or saddle member. A yoke member would be configured with slots or other structures to receive the flanges 322 of the cap member 321 and thereby maintain the vertical positioning of the upper cap member 321 within the yoke so that rotation of the cap member can apply a downward force upon the saddle member 325, which is held in a stable orientation against the spinal rod as the cap member 231 is rotated.

Figure 19:
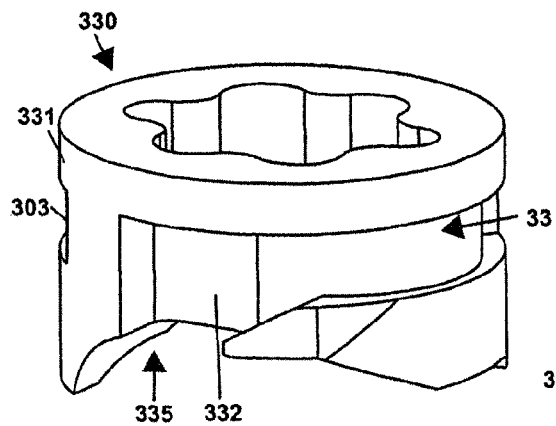
FIG. 19 is an alternative slotted locking member with a lower camming surface that may be adapted for use with the invention.

The locking member may alternatively be provided with slots rather than flanges, so that it is capable of interlocking with a yoke having flanges or posts configured to interlock with the slots of the locking member. For instance, FIG. 19 shows one alternative locking member 330 having a generally cylindrical body 331 with a pair of horizontal slots 333 and a lower camming surface 335. A relatively large mouth region 332 is provided as a lead-in to the horizontal slot in order to receive and facilitate proper orientation of flanges or posts of the yoke member. Rotation of the locking member 330 so that the flanges or posts of the yoke member travel along the slot 333 rotates the lower camming surface 335 into an orientation that exerts a downward force upon a spinal rod, and interaction between the slots 333 and the yoke member prevents the cap member from escaping the yoke.

Figure 20:
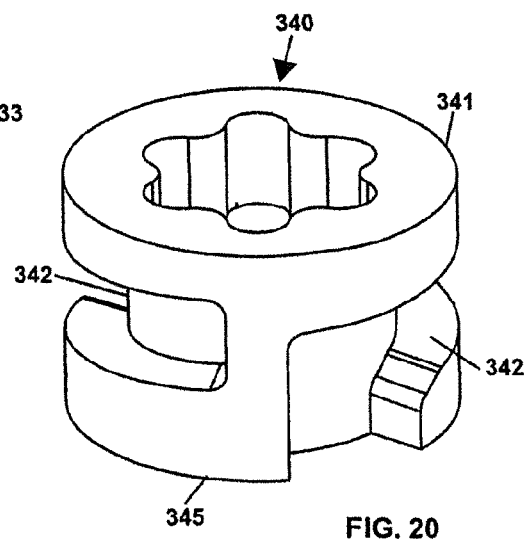
FIG. 20 is an alternative locking member with angled slots that may be adapted for use with the invention.

FIG. 20 shows an alternative locking member 340 similar to that of FIG. 19, except that a pair of slots 342 in the side of the generally cylindrical body 341 are sloped to cam against flanges or posts of a yoke member. As a result, the bottom surface 345 of the cap member is flat, and is not configured to create a camming action when rotated against the surface of a spinal rod. A large mouth region 343 facilitates aligning yoke structures in the slots 342.

Figure 21A:
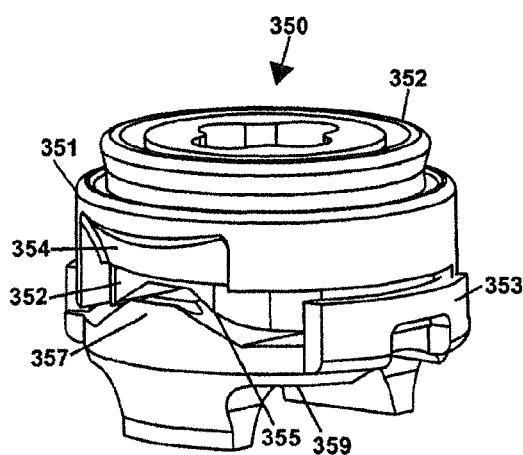
FIG. 21A and 21B are views of an alternative multi-part locking member configured to be snap-locked into a partially flexible yoke member that may be adapted for use with the invention.
Figure 21B:
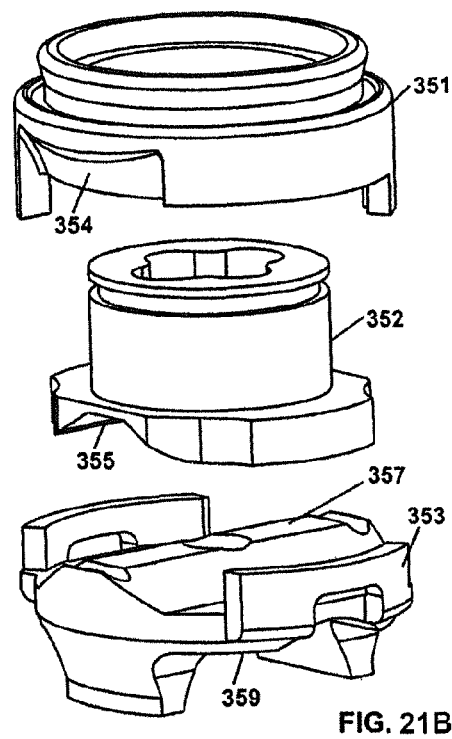

Yet another alternative locking cap member 350 is illustrated in FIGS. 21A and 21B. This cap member is intended for use with a yoke member configured to receive the cap in a snap-lock manner. As a result, the yoke member preferably will be provided with resiliently flexible arm portions that allow the cap member to slide into place in one direction but hold the cap member against shifting in the opposite direction, as described in detail in U.S. Published Application 2008/0045955, which is hereby fully incorporated by reference. Although the cap member may be configured as a simple plug that snap-locks into a yoke upon linear insertion, in the illustrated form the locking member 350 includes three separate primary components: a collar 351, a cam lock member 352, and a saddle member 353. When the cap member 350 is linearly inserted into an appropriately configured yoke member, the collar 351 will snap-lock in place, preventing the cap member from disengaging from the yoke. The saddle member 353 has a lower surface 359 configured to be seated upon a spinal rod, and a contoured upper surface 357 configured to mate in one orientation with a lower contoured surface 355 of the cam lock member 352 that is positioned between the collar and saddle members. Rotation of the cam lock member 352 relative to the collar member 351, which remains stationary relative to the yoke, and the saddle member, which is seated against the spinal rod, causes camming action between the contoured lower surface 355 of the cam lock member 352 and the upper contoured surface 357 of the saddle member 353, forcing the cam lock member and saddle member apart and driving the saddle member downward against the spinal rod to lock the rod in place within the yoke.

While there have been illustrated and described particular embodiments of the present invention, it will be appreciated that numerous changes and modifications will occur to those skilled in the art, and it is intended in the appended claims to cover all those changes and modifications which fall within the true spirit and scope of the present invention.

What is claimed is:

1. A method of securing an elongate member to a vertebra, the method comprising, in any order:
    disposing a head of an anchor member in a lower yoke member so that a head portion of the anchor member is seated against an interior surface of the lower yoke member and a body portion of the anchor member extends through an opening in the lower yoke member;
    rotatably coupling the lower yoke member to an upper yoke member at a rotatable coupling therebetween;
    securing the anchor member to a surface of a vertebra;
    pivoting the lower yoke member to position the lower yoke member with respect to the anchor member;
    rotating the upper yoke member relative to the lower yoke member so that the upper yoke member is at a desired rotational position with respect to the lower yoke member;
    positioning an insert member within the upper and lower yoke members with lower flexible portions of the insert member engaged against the head of the anchor member;
    disposing an elongate member in a channel of the upper yoke member so that the elongate member is positioned at the second angle with respect to the body of the anchor member; and
    inserting a lock member into the upper yoke member and locking the lock member in place such that locking of the lock member within the upper yoke member fixes the position of the elongate member relative to the upper yoke member, fixes the rotational position of the upper yoke member relative to the lower yoke member, fixes the position of the lower yoke member relative to the anchor member, and urges the insert member lower flexible portions to flex radially outward into tight engagement with one of the upper and lower yoke members at the rotatable coupling therebetween,
    wherein a single instrument is used to perform the steps of pivoting the lower yoke member with respect to the anchor member and rotating the upper yoke member relative to the lower yoke member.

2. The method of claim 1 wherein the step of rotatably coupling the upper yoke member to the lower yoke member is performed before the steps of disposing the head of anchor member in the lower yoke member and disposing the elongate member in the channel of the upper yoke member.

3. The method of claim 1, wherein rotatably coupling the lower yoke member to the upper yoke member comprises inserting tabs of the upper yoke member into one or more recesses of the lower yoke member to form the rotatable coupling, and the insert member lower flexible portions are urged into tight engagement with the upper yoke member tabs to maintain the upper yoke member tabs within the one or more recesses of the lower yoke member.

4. The method of claim 1 wherein the lower yoke member is pivoted by rotating a first handle of the single instrument and the upper yoke member is rotated by rotating a second handle of the single instrument.

5. The method of claim 1 wherein the upper yoke member is rotated relative to the lower yoke member by receiving the upper and lower yoke members in a head portion of the single instrument with the lower yoke member non-rotatably received therein and a positioner of the head portion non-rotatably received in the upper yoke member channel, and turning a handle member of the single instrument connected to the positioner causes the positioner to rotate which causes the upper yoke member to rotate while the lower yoke member remain stationary in the head portion.

6. The method of claim 5 wherein the lower yoke member opening is a bottom slot opening that extends to only one side of the lower yoke member allowing the anchor member body portion to generally be pivoted in a plane in the slot opening, and wherein the lower yoke member is pivoted to position the lower yoke member with respect to the anchor member by another handle member of the single instrument connected to the head portion causing the head portion and the lower yoke member non-rotatably received therein to rotate for adjusting the plane of pivoting of the anchor member body portion in the lower yoke member slot opening.

7. The method of claim 6 wherein turning the handle members includes turning indicia associated therewith with indicium associated with the handle that rotates the upper yoke member providing an indication of the orientation of the upper yoke member channel and the indicium associated with the handle that rotates the lower yoke member providing an indication of the orientation of the plane of pivoting provided by the lower yoke member slot opening.

8. The method of claim 5 wherein the head portion and the lower yoke member are configured so that the lower yoke member is only allowed to be received in the head portion in a single orientation therein, and the lower yoke member is received in the head portion by aligning the lower yoke member and the head portion to allow the lower yoke member to be received in the head portion in the single orientation thereof.

* * * * *